United States Patent [19]
Uggeri et al.

[11] Patent Number: 6,149,890
[45] Date of Patent: Nov. 21, 2000

[54] CHELATED COMPLEXES OF PARAMAGNETIC METALS WITH LOW TOXICITY

[75] Inventors: Fulvio Uggeri; Franco Fedeli; Alessandro Maiocchi; Maurizio Franzini; Mario Virtuani, all of Milan, Italy

[73] Assignee: Dibra S.p.A., Milan, Italy

[21] Appl. No.: 09/061,036

[22] Filed: Apr. 16, 1998

[30] Foreign Application Priority Data

Apr. 18, 1997 [IT] Italy .................................. MI97A0930

[51] Int. Cl.⁷ .......................... A61B 5/055; C07D 225/00; C07F 5/00
[52] U.S. Cl. ....................... 424/9.263; 540/465; 540/474; 534/16; 534/10; 534/14; 534/15
[58] Field of Search .......................... 424/9.363; 540/474, 540/455; 534/16

[56] References Cited

U.S. PATENT DOCUMENTS 5,747,000 5/1998 Platzek et al. ..................... 424/9.363

*Primary Examiner*—Mukund J. Shah
*Assistant Examiner*—Pavanaram K Sripada
*Attorney, Agent, or Firm*—Nixon & Vanderhye

[57] ABSTRACT

Compounds of formulae (I) and (II)

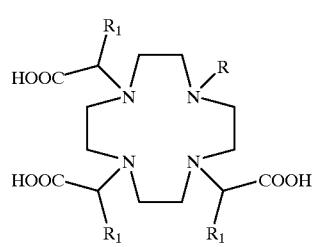

(I)

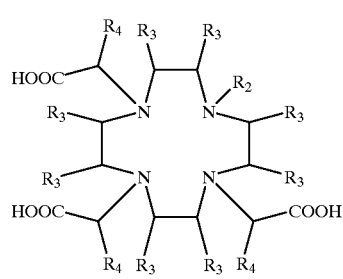

(II)

wherein the R, $R_1$, $R_2$, $R_3$ and $R_4$ groups have the meanings defined in the disclosure, are useful chelants for metal ions. The complexes of compounds (I) and (II) with paramagnetic ions are useful as contrast agents for M.R.I. imaging.

8 Claims, No Drawings

CHELATED COMPLEXES OF PARAMAGNETIC METALS WITH LOW TOXICITY

The present invention relates to the field of the diagnostic technique known as Magnetic Resonance Imaging (M.R.I.), a renowned, powerful diagnostic procedure used in medical practice to detect anomalies in organs or tissues of the human or animal body (see: Rocklage S. M., Watson A. D. and Carvlin M. J., Magnetic Resonance Imaging, Chap. 14, Vol. 1, Second Ed., 1992; Stark D. D. and Bradley W. G. Eds.). Particularly, the invention relates to novel compounds able to chelate paramagnetic metal ions, to their chelated complexes and to the physiologically acceptable salts thereof as well as the use of these compounds as M.R.I contrast agents.

Lanthanide ions are known to be among the most toxic paramagnetic metal ions in vivo. It is therefore necessary to administer said ions in the form of chelated complexes to the subject undergoing such a diagnostic procedure, as chelation by an electron donor ligand appreciably decreases the toxicity of the metal ion. On the other hand, this often also decreases undesirably the relaxivity properties, as accessibility by the water protons to the inner coordination sphere of the metal ion is reduced. The relaxivity of a chelated complex is generally significantly lower than that of the corresponding metal ion (The British Journal of Radiology, 68, 225–247, 1995).

It is therefore important for the paramagnetic chelated complex to have a high stability, i.e. a high thermodynamic stability constant, in order to have a low toxicity. A higher stability can be obtained, for example, using macrocyclic ligands, in which the metal ion is incorporated in a rigid structure; Gd-DOTA (Dotarem®) or Gd-HP-DO3A (ProHance®) are, for example, known to have a higher stability than Gd-DTPA (Investigative Radiology, 27 (Suppl.1), S1–S6, 1992; Topics in Magnetic Resonance Imaging, 7(3), 181–195, 1995). Gd-DOTA and Gd-HP-DO3A are macrocyclic ligand contrast agents commercially available at present.

The thermodynamic stability being the same, other factors affecting the toxicity of a contrast agent are the osmolality of the solution (in case of injectable formulations) and the intrinsic toxicity of the molecule, or molecular toxicity (Toxicology Letters, 64/65, 705–715, 1992). The osmolality of the solution particularly affects the toxicity of the contrast agent after intravenous administration; the molecular toxicity should, in its turn, be specifically considered when the contrast agent is administered to patients with impaired permeability of the blood-brain barrier, for example patients affected by cerebrovascular disorders, cerebral metastases, traumas and the like, in that the contrast agent can enter the tissues of central nervous system (Investigative Radiology, 25, S49–S50, 1990; M. Nadjmi Ed., XVth Congress of the European Society of Neuroradiology, Würzburg, Sept. 13–17th, 1988, 581–584 —Springer-Verlag Berlin Heidelberg 1989); this can, in fact, result in the appearance of even remarkable neurotoxic effects. Molecular toxicity can be evaluated by tests carried out either in vitro (histamine release, inhibition of enzymatic activity and of coagulation); or in vivo, administering the compound directly to the nervous tissue, which is the substrate most sensitive to molecular toxicity.

$DL_{50}$ values after intracerebral administration (intracisternal, intracerebroventricular), for example in the mouse and in the rat, can therefore be taken as a highly sensitive index of the molecular toxicity of the contrast agent (Toxicology Letters, cited ref.). In particular, the intracerebroventricular administration seems to be the most sensitive to discriminate the neurotoxicity of the compounds (Proceedings of the 10th National Congress of the Italian Toxicology Society, Pavia, September 21–24th, 100, 1994).

The "neurotoxicity index" is defined by the following ratio:

$$\text{neurotoxicity index} = \frac{DL_{50} \text{ i.v.}}{DL_{50} \text{ i.c.}}$$

It is evident that, $DL_{50}$s values after intravenous administration being the same, the higher the $DL_{50}$ value after intracerebral administration, the lower the neurotoxicity index of the compound.

Generally speaking, open-chain paramagnetic chelates have a cerebral toxicity different than the corresponding macrocyclic chelates; in particular, chelates such as Magnevist® (gadopentetate dimeglumine) and Omniscan® (gadodiamide) showed a better tolerability, after intracisternal administration, than such macrocyclic chelates as Dotarem® (gadoterate), gadobutrol and ProHance® (gadoteridol) (European Journal of Radiology, 21, 1–10, 1995).

Researches in the field of M.R.I. contrast agents are therefore directed to discovery of chelating agents having a high stability to paramagnetic metal ions, with a consequent decrease in toxicity deriving from the release of the free metal ion, which keep a good relaxivity and a low effective dose and which, above all in case of specific uses, have a low neurotoxicity index. This proves of paramount importance when the administration of high doses of contrast agent is necessary in order to improve the imaging of some lesions, such as infections, metastases or cerebral neoplasms, subacute cerebral infarction, head and neck tumors (Topics in Magnetic Resonance Imaging, 7(3), 181–195, 1995; The British Journal of Radiology, 68, 225–247, 1995).

The present invention relates to chelated complexes of paramagnetic metals characterized by an extremely favourable neurotoxicity profile. In particular, the paramagnetic chelated complexes of the present invention showed, after intracerebroventricular administration to the mouse, extremely high $DL_{50}$ values compared with the teachings of the prior art. The compound described in example 1 (gadolinium complex of 10-[2-[[2-(2-hydroxyethoxy)ethyl]amino]-2-oxoethyl]-α,α',α''-tris(hydroxymethyl)-1,4,7,10-tetraazacyclododecane-1,4,7-triacetic) acid has, for example, a $DL_{50}$ of 0.23 mmol/kg after intracerebroventricular administration to the mouse. The compounds described in example 2 (gadolinium complex of α,α',α''-tris(hydroxymethyl)-10-(2-hydroxypropyl)-1,4,7,10-tetraazacyclododecane-1,4,7-triacetic acid) and in Example 4 (Na⁺Gd[THM-DOTA]⁻) have a very good tolerability as well, with a $DL_{50}$, after intracerebroventricular administration to the mouse, of 0.170 and 0.150 mmol/kg, respectively; the corresponding value for Gd-DOTA being 0.064 mmol/kg. This strongly suggests the possible use of the compounds of the present invention for imaging of cerebral lesions such as tumors, metastases, in highly safe conditions for the patient.

The present invention relates to the compounds of formula (I), both in the racemic and optically active forms:

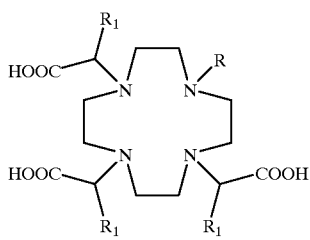

(I)

wherein:
- R is a ($C_1$–$C_{15}$) straight or branched alkyl chain, optionally interrupted by one or more oxygen, nitrogen, sulfur atoms, as well as by —CO—, —CONH—, —NHCO—, —SO—, —$SO_2$—, —$SO_2$NH— groups, or optionally substituted by one or more $NH_2$, OH, halogen, COOH groups and corresponding ester or amide derivatives; said chain being optionally interrupted and/or substituted by one or more 5- or 6-membered cyclic, saturated, carbocyclic or heterocyclic groups, in which said cyclic groups are optionally substituted by one or more X groups, which can be the same or different, in which
- X is —OH, halogen, —$NH_2$, —$NHR_5$, —$N(R_5)_2$, —O—$R_5$, —S—$R_5$, —CO—$R_5$, wherein $R_5$, which can be the same or different, are a ($C_1$–$C_5$) straight or branched alkyl, optionally substituted by one or more hydroxy, alkoxy, carboxy groups, or X is a COOH group, or an ester or amide derivative thereof, or a —$SO_3$H group or an amide derivative thereof,
- $R_1$, which can be the same or different, are a hydrogen atom or a —$CH_2$OH group, with the provisos that:
R is different from: unsubstituted alkyl, —$CH_2$COOH,

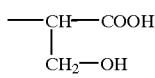

at least two of the $R_1$ substituents are —$CH_2$OH.

The invention also relates to the compounds of formula (II), both in the racemic and optically active forms:

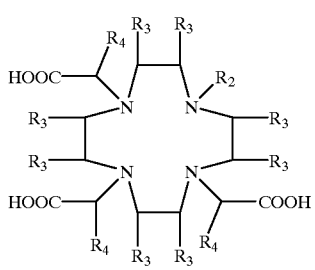

(II)

wherein:
- $R_2$ is a hydrogen atom, or a ($C_1$–$C_{15}$) straight or branched alkyl chain, saturated or unsaturated, optionally interrupted by one or more oxygen, nitrogen, sulfur atoms, as well as by —CO—, —CONH—, —NHCO—, —SO—, —$SO_2$, —$SO_2$NH— groups, or optionally substituted by one or more $NH_2$, OH, halogen, COOH groups and corresponding ester or amide derivatives; said chain being optionally interrupted and/or substituted by one or more 5- or 6-membered cyclic, carbocyclic or heterocyclic groups, in which said cyclic groups are optionally substituted by one or more X groups, which can be the same or different, in which
- X is —OH, halogen, —$NH_2$, —$NHR_5$, —$N(R_5)_2$, —O—$R_5$, —S—$R_5$, —CO—$R_5$, wherein $R_5$, which can be the same or different, are a ($C_1$–$C_5$) straight or branched alkyl, optionally substituted by one or more hydroxy, alkoxy, carboxy groups, or X is a COOH group, or an ester or amide derivative thereof, or a group —$SO_3$H or an amide derivative thereof,
- $R_3$, which can be the same or different, are a hydrogen atom or a —$CH_2$OH group,
- $R_4$, which can be the same or different, have the same meanings as described for $R_3$ or are $CH_3$ or $C_2H_5$, with the proviso that at least two $R_3$ are —$CH_2$OH.

Within formula (II), a class of particularly preferred compounds comprises those of formula (III):

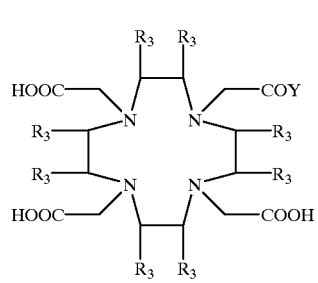

(III)

wherein:
- Y is a —OH group or a —$N(R_6)_2$ group, in which $R_6$ groups, which can be the same or different, are a hydrogen atom or a ($C_1$–$C_{15}$) straight or branched alkyl chain, optionally interrupted by one or more oxygen, nitrogen atoms, as well as by —CO—, —CONH—, —NHCO—, —SO—, —$SO_2$—, —$SO_2$NH— groups, or optionally substituted by one or more $NH_2$, OH, COOH groups and corresponding ester or amide derivatives, or the two $R_6$ groups, taken together, form a cyclic unit, comprising the amide nitrogen atom, being said cyclic unit optionally interrupted by one or more oxygen and/or nitrogen atoms and optionally substituted by one or more X groups, which can be the same or different, wherein X has the same meanings as described for the compounds of formula (II);
- $R_3$, which can be the same or different, are a hydrogen atom or a —$CH_2$OH group;

with the proviso that at least two $R_3$ are —$CH_2$OH.

Objects of the invention also are:
the optically active forms of the compounds of formulae (I), (II) and (III), when chiral centres are present;
chelated complexes of the compounds of formulae (I), (II) and (III) with the ions of metallic elements having atomic numbers ranging from 20 to 31, 39, from 42 to 44, 49 and from 57 to 83, among which particularly preferred are: Gd(III), Mn(II), Fe(II), Fe(III), Cu(II), Cr(III), Eu(III), Dy(III), La(III), Yb(III);
the salts thereof with physiologically acceptable organic bases selected from primary, secondary, tertiary amines or basic amino acids, or with inorganic bases the cations of which are sodium, potassium, magnesium, calcium, or mixtures thereof, or with anions of physiologically acceptable organic acids, or with anions of inorganic acids such as hydrogen halides.

It is also an object of the invention the use of the compounds of formulae (I), (II) and (III) and of the complex salts thereof for the preparation of pharmaceutical compositions for the diagnostic use, as well as the formulations themselves.

In compounds of formula (I), particularly preferred meanings for R are the following:

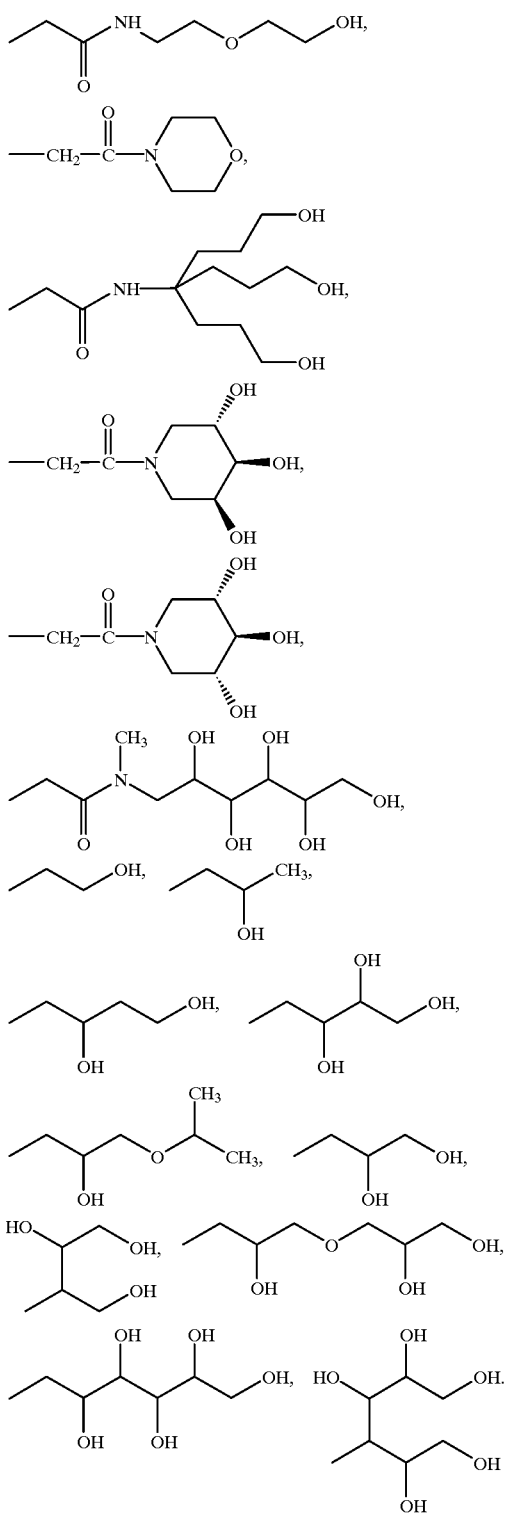

In compounds of formula (II), particularly preferred meanings for $R_2$ are the following:

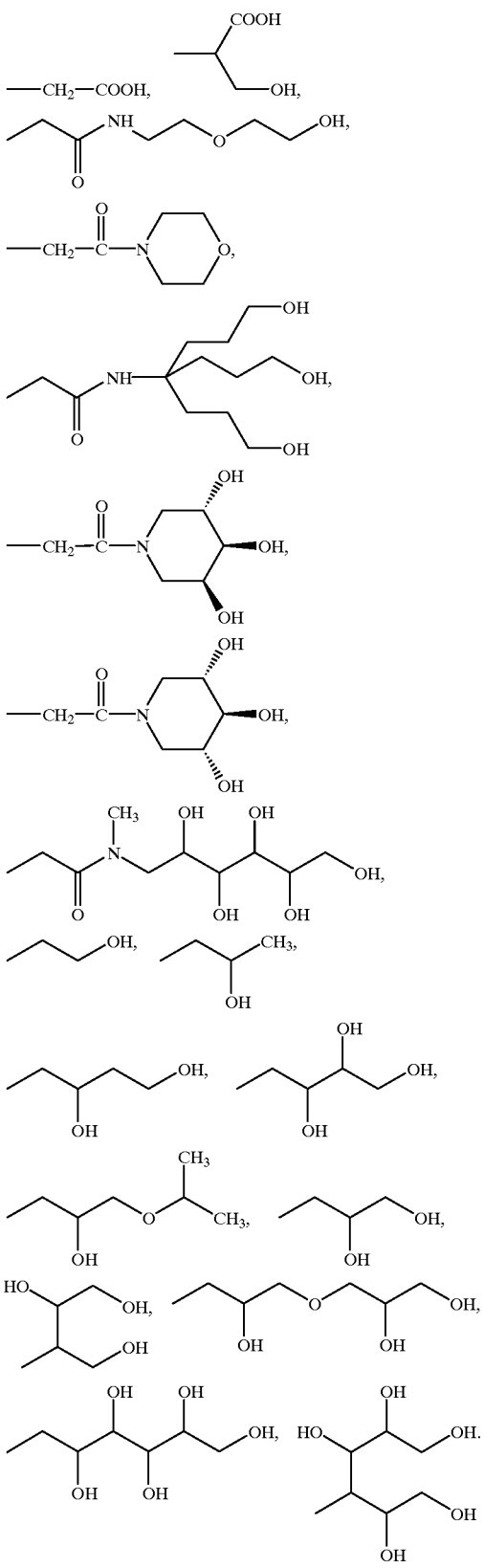

In compounds of formula (III), particularly preferred meanings for Y are the following:

—OH, —NH—CH$_2$—CH$_2$—O—CH$_2$—CH$_2$—OH,

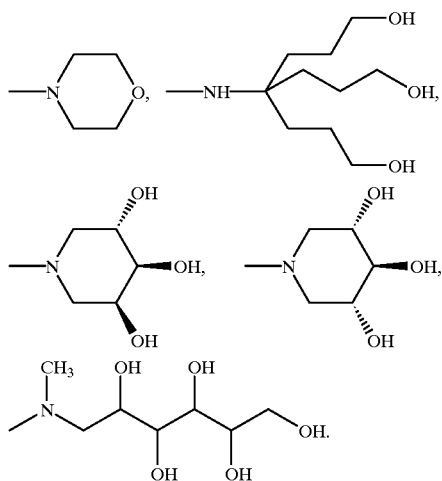

The compounds of the invention are valuable for use in a number of different fields. Non limiting examples of the uses thereof are: recovery, separation, selective extraction of metal ions; use in therapy as detoxifying or radiotherapy agents; use as contrast agents for the in vivo or in vitro diagnosis through magnetic resonance, X-rays, ultrasounds or scintigraphy.

As M.R.I. contrast agents, preferably used are the chelated complexes of the chelating agents of general formulae (I) to (III) with divalent or trivalent ions of elements having atomic numbers ranging from 21 to 29, 39, 42, 44, or from 57 to 71; Fe$^{(2+)}$, Fe$^{(3+)}$, Cu$^{(2+)}$, Cr$^{(3+)}$, Gd$^{(3+)}$, Eu$^{(3+)}$, Dy$^{(3+)}$ or Mn$^{(2+)}$ being preferred; Gd$^{(3+)}$, Mn$^{(2+)}$, Dy$^{(3+)}$ and Fe$^{(3+)}$ being particularly preferred.

For use in X-ray or ultrasound imaging, the chelated metal species is preferably a heavy metal, for example a non-radioactive metal with atomic number higher than 37.

For use in scintigraphy and radiotherapy, the chelated metal species is a radioisotope, such as $^{51}$Cr, $^{68}$Ga, 111In, $^{99m}$Tc, $^{140}$La, $^{168}$Yb.

For use in the detoxication from heavy metals, the ligands of the invention can be administered in the form of salts with physiologically acceptable ions, such as Na$^+$, Ca$^{++}$, NH$_4$+, Zn$^{++}$, or as meglumine salts.

For the uses mentioned above, the compounds of the invention can be used as such, or they can be conjugated with macromolecules or incorporated in structures which carry them to specific body sites.

In case the chelated complex has a total charge, this is preferably neutralized with a physiologically acceptable counter-ion. Among the substances suitable for salifying the compounds of the invention and/or their chelated complexes, the following can be cited:

anions of physiologically acceptable inorganic acids, such as hydrogen halides (chlorides, bromides, iodides) or other ions such as sulfate;

anions of organic acids commonly used in the pharmaceutical technique for the salification of basic substances, such as acetate, succinate, citrate, fumarate, maleate, oxalate;

cations of inorganic bases such as ions of alkali or alkaline-earth metals selected from sodium, potassium, magnesium, calcium, and/or mixtures thereof;

cations of physiologically acceptable organic bases selected from primary, secondary and tertiary amines such as ethanolamine, diethanolamine, morpholine, glucamine, N-methylglucamine, N,N-dimethylglucamine;

cations and anions of amino acids such as lysine, arginine and ornithine, or of aspartic and glutamic acids.

Particularly preferred are N-methylglucamine salts.

As far as the administration route is concerned, the compounds of the present invention can be administered by the intravasal (for example intravenous, intraarterial, intracoronaric, intraventricular etc.), intrathecal, intraperitoneal, intralymphatic, intracavital and intraparenchymal routes. They are also suitable for the oral or enteral administration (specifically for the imaging of the gastrointestinal tract) or for the direct injection into a body cavity having a canal communicating with the outside (for example uterus, bladder).

Particularly preferred are anyway the intravasal and, above all, the intrathecal routes, thanks to the unique characteristics of tolerability of the compounds of the invention.

They can be formulated with additives conventionally used for the pharmaceutical or veterinary formulations, for example stabilizers, antioxidants, osmolality and pH adjusters, buffers and the like.

For the parenteral administration, they are preferably formulated as sterile aqueous solutions or suspensions, whose pH can range from 6.0 to 8.5. Said aqueous solutions or suspensions can be administered in concentrations ranging from 0.002 to 1.0 M.

These formulations can also be lyophilized and supplied as such, or for reconstitution before use. For the gastrointestinal use or for the injection into body cavities, these agents can be formulated as a solution or suspension containing suitable additives in order to, for example, control viscosity.

For the oral administration they can be formulated according to preparation methods routinely used in the pharmaceutical technique, optionally also as coated formulations to gain extra protection from the acid pH of stomach, thereby inhibiting the release of the chelated metal ion, which usually occurs at the typical pH values of gastric juices.

Other excipients, such as sweeteners and/or flavours, can also be added according to known techniques of pharmaceutical technique.

The solutions or suspensions of the compounds of this invention can also be formulated as aerosol for use in aerosol-bronchography.

The compounds of formula (I) can preferably be prepared according to the following general synthetic scheme:

SCHEME 1

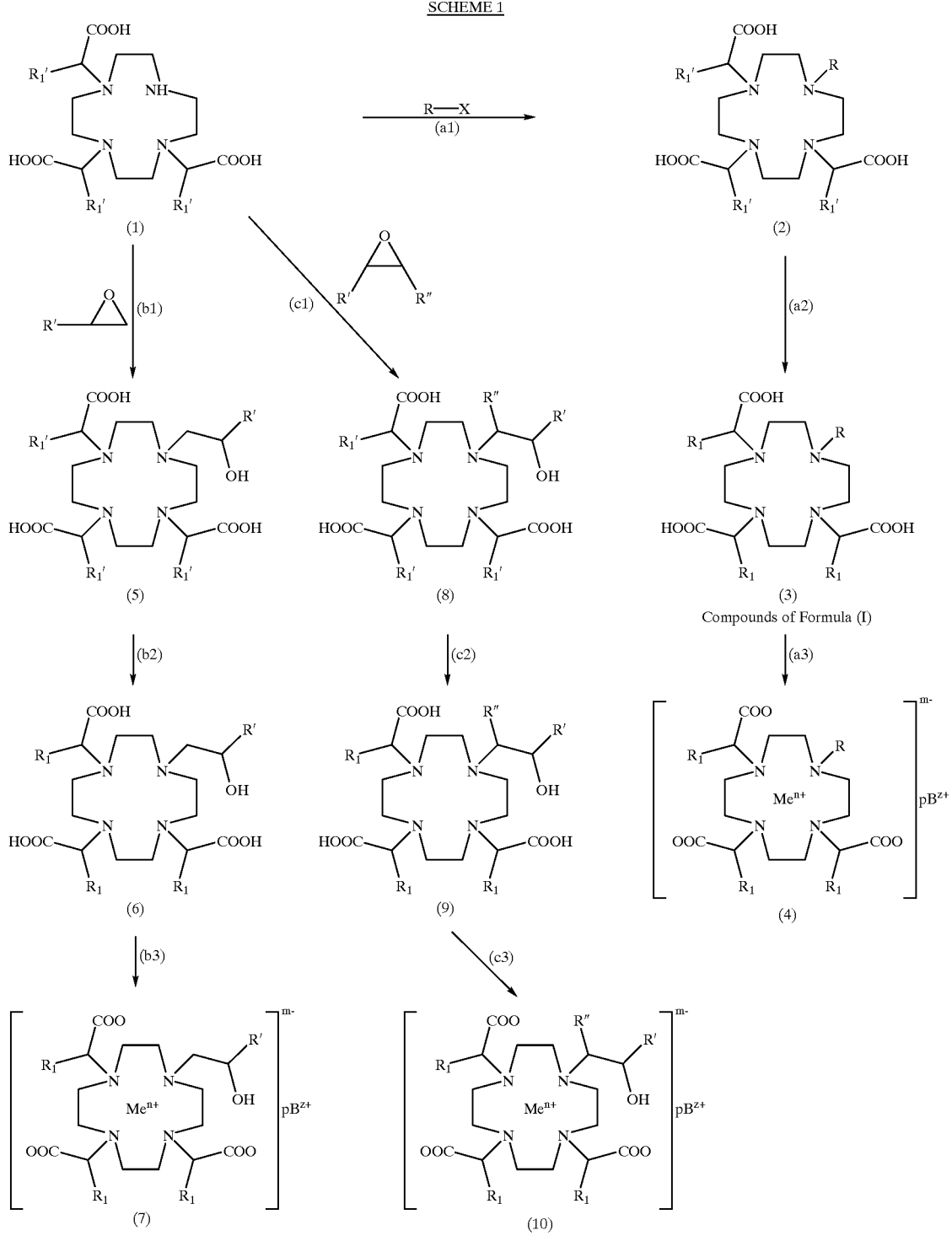

wherein:
$R_1'$=H or —$CH_2$—OPg, wherein Pg is a protective group, for example benzyl;
R, $R_1$ are as defined above for the compounds of formula (I);
X=Cl, Br, I;
The starting product is a compound of formula (1), prepared according to what described in WO 89/05802, wherein the hydroxy groups are protected by a suitable group, for example (in the described case) benzyl. In step:
(a1) said product is reacted with compound R-X, wherein R is the group to be substituted at the tetraazacyclododecane nitrogen and X is an appropriate leaving group, for example Cl, Br; the reaction is preferably carried out in $H_2O$ or DMF, at temperatures from 20 to 100° C., thereby obtaining compound of formula (2) which, in step (a2) is deprotected by catalytic hydrogenation, which can be carried out in water with Pd/C at room temperature, to give the desired ligand (3), which, in step (a3) is reacted with the stoichiometric amount of metal, in the form of salt or oxide, optionally in the presence of the amount of acid or base necessary for the neutralization; the reaction being preferably effected in water or in a suitable water-alcohol mixture, at temperatures from 25 to 100° C., preferably from 40 to 80° C.; thereby obtaining the chelated complex (4), in which:

$Me^{n+}$=ion of the metallic element having atomic number ranging from 20 to 31, 39, from 42 to 44, 49 and from 57 to 83 (for ex. $Gd^{3+}$);

n=number of the positive charges of said ion;

m=number of the total charges of the chelated complex;

B=substance able to salify the chelated complex (for example $Na^+$, $K^+$, $Mg^{++}$, $Ca^{++}$ or mixtures thereof, meglumine, etc.);

z=number of the charges of B;

p is a number so that the product: p·z=m.

In case the product of formula (I) is a compound in which R is a mono- or polyhydroxyalkyl chain unsubstituted at the carbon atom adjacent to the macrocycle nitrogen, a different synthetic route can be followed, in which, in step (b1) compound (1) is reacted in basic medium (for ex. KOH) with a suitable epoxide, in which R' can be, for example: H, —$CH_3$, —$CH_2OH$, —$CH_2$—$CH_2OH$, —CHOH—$CH_2OH$, —CHOH—CHOH—$CH_2OH$,

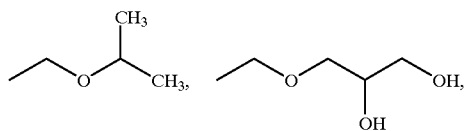

to obtain compound (5) which, in step (b2) is deprotected at the hydroxyls according to what described in step (a2); the resulting compound (6) is reacted in step (b3) with the suitable salt or oxide of the desired metal, according to the general procedure described above, to give the corresponding chelated complex (7).

On the other hand, in case compound of formula (I) is a compound in which R is a mono- or polyhydroxyalkyl chain substituted at the carbon atom adjacent to the macrocycle nitrogen, in step (c1) compound (1) is reacted in basic medium (for ex. KOH) with a suitable epoxide, in which R' and R" have independently the meanings described above for R', except for H, to obtain compound (8) which, after deprotection and complexation, gives the final compound (10).

Concerning the preparation of the compounds of formulae (II) and (III), the synthetic route differs depending on the positions on the ring at which the hydroxymethyl substituents are to be introduced. The following synthetic routes can be used:

1) Synthesis known as "crab-like" (Tetrahedron Letters, 31, 1077–1080, 1990; Synlett, 611–620, 1993).

The general scheme for the synthesis of the ligand described in example 3 and of the its analogues is reported in the following:

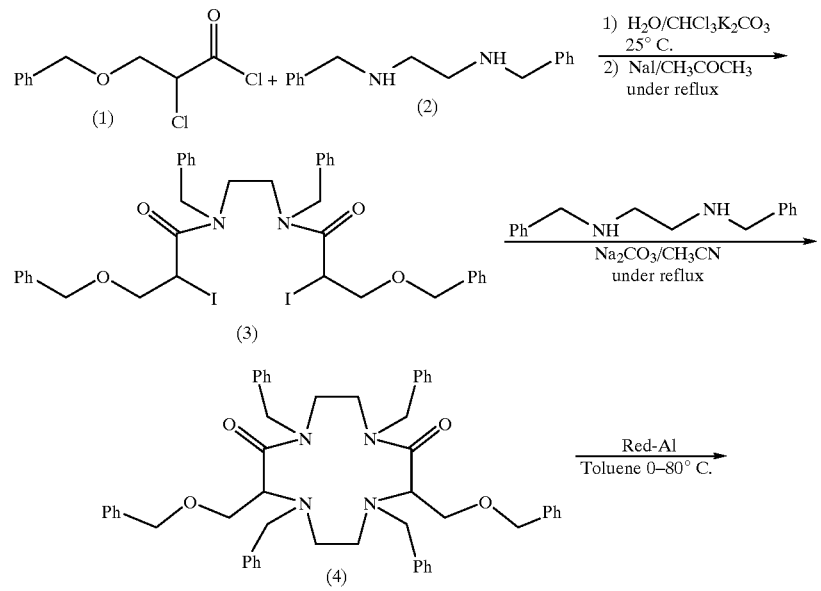

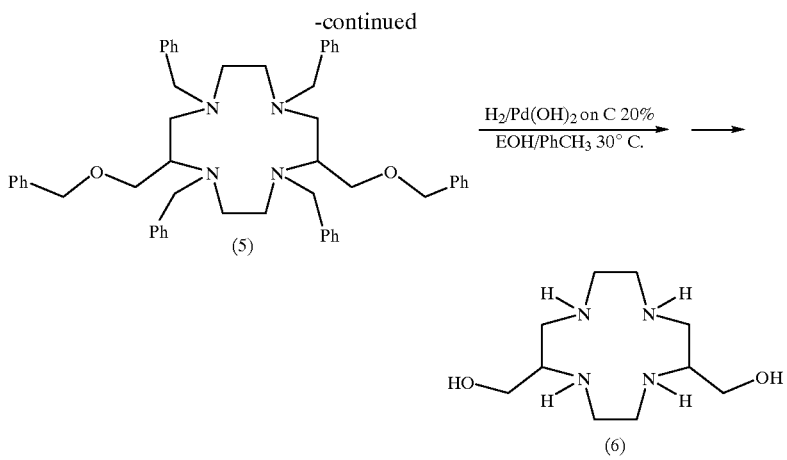

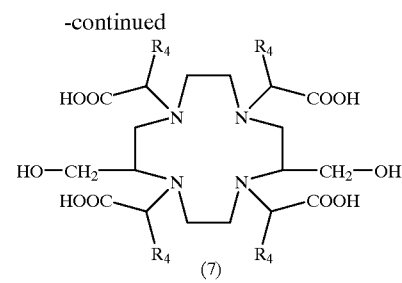

wherein $R_4$ is as defined above for the compounds of formula (II).

2) Tetramerization of a suitably substituted N-benzylaziridine.

The general scheme for the synthesis of the ligand described in example 4 and of the derivatives thereof is reported below:

The starting compound is 2-chloro-3-hydroxy-propionic acid chloride (1), wherein the hydroxyl is protected by a suitable group, preferably benzyl. This compound is reacted with bis(phenylmethyl)ethylene-diamine (2) and NaI, to give the intermediate (3) which, by reaction with bis(phenylmethyl)ethylenediamine, cyclizes, yielding the intermediate (4). This is reduced at the carbonyl groups, to give compound (5) which, upon deprotection of the hydroxyls, gives intermediate (6).

Intermediate (6) is then alkylated with the α-halo derivative of a suitable carboxylic acid, to obtain the desired ligand (7), which is subsequently subjected to complexation with the suitable metal and optionally to salification:

SCHEME 3

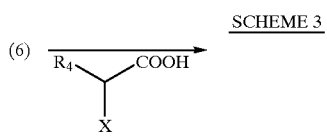

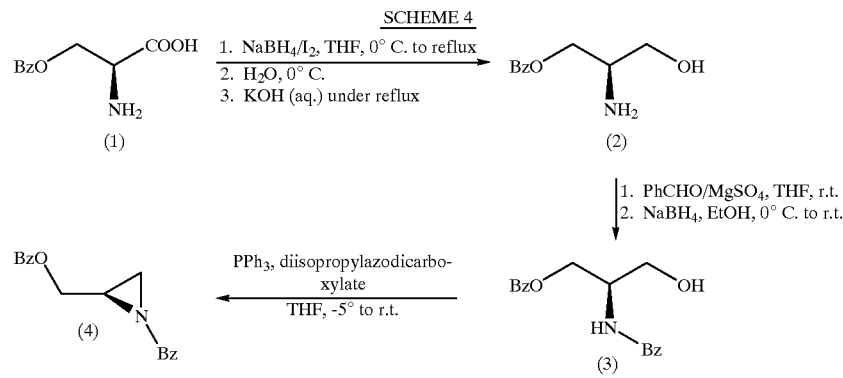

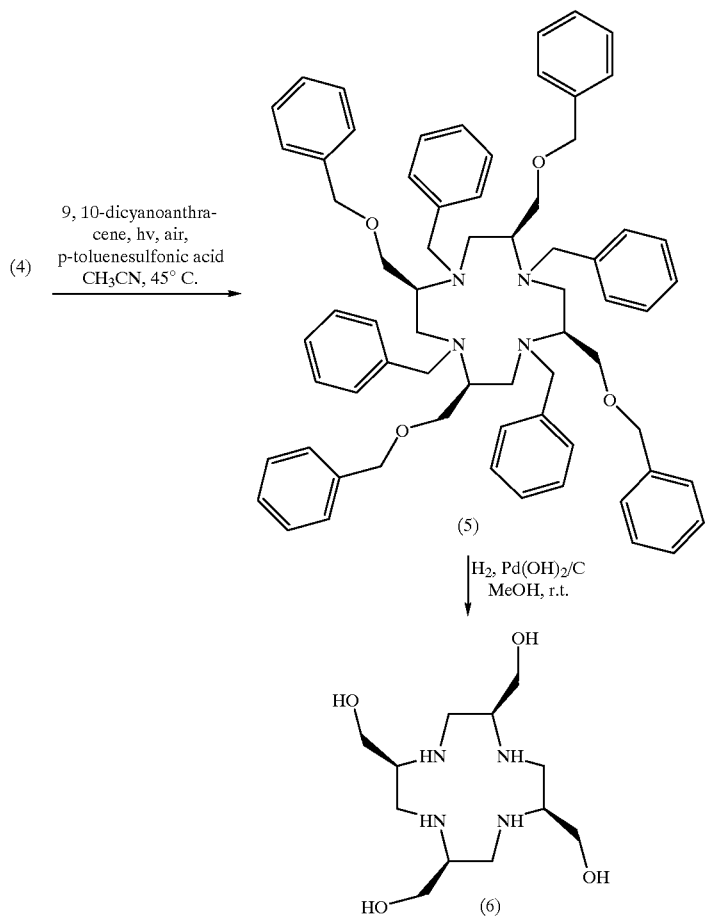

wherein Bz=benzyl.

The cyclotetramerization of (R)-2-[(phenylmethoxy)methyl]-1-(phenylmethyl)aziridine (4) to give compound (5) is based on a photoinduced electron transfer mechanism by means of light emitted by a high-pressure mercury-vapor lamp, shielded from radiations of wavelength below 300 nm by a Pyrex filter; the reaction takes place in the presence of an oxidizing photochemical sensitizer, such as 9,10-dicyanoanthracene, and of catalytic amounts of an acid, such as 4-toluenesulfonic acid, at a temperature from room temperature to 60° C. The reaction is preferably carried out in acetonitrile; alternatively, methanol or, preferably, an acetonitrile/methanol mixture, can be used.

The resulting compound (5) is debenzylated by catalytic hydrogenation in the subsequent step, to give intermediate (6), which is alkylated with the α-halo derivative of a suitable carboxylic acid, to obtain the desired ligand (7), which is subsequently complexed with the suitable metal and, optionally, salified:

SCHEME 5

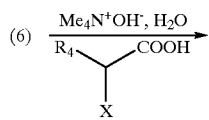

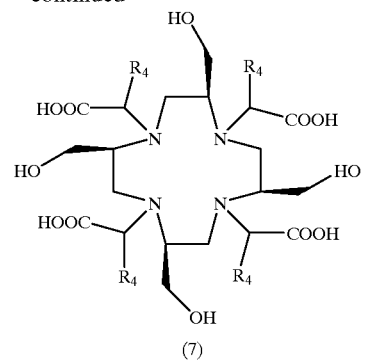

wherein $R_4$ is as defined above for compounds of formula (II).

Examples of cyclotetramerization of N-benzylaziridine exist in literature.

1. WO 95/31444, Example 7(C), discloses the synthesis of [2S-(2α,5α,8α,11α)]-2,5,8,11-tetramethyl-1,4,7,10-tetra-(phenylmethyl)-1,4,7,10-tetraazacyclododecane by cyclotetramerization of [S]-N-benzyl-2-methyl-aziridine with p-toluenesulfonic acid in ethanol as catalyst, at room temperature for 64–48 hours, followed by purification through column chromatography and alkalinization with $NH_4OH$.
2. 1,4,7,10-Tetrabenzyl-1,4,7,10-tetraazacyclododecane was obtained by refluxing a mixture of N-benzylaziridine and p-toluenesulfonic acid in 95% ethanol for 6 hours (J. Heterocycl. Chem., 5(2), 305, 1968).

3. 1-Benzyl-2-(R)-ethylaziridine, by treatment with BF₃Et₂O for 20 hours at r.t., gave 1,4,7,10-tetrabenzyl-2,5,8,11-tetra-(R)-ethyl-1,4,7,10-tetraazacyclododecane; the same compound was obtained refluxing 1-benzyl-2-(R)-ethylaziridine in benzene or ethanol, for 24 hours, with the same catalyst (Tetrahedron Letters, 16, 1367–1370, 1970).

4. N-(Phenylethyl)aziridine, p-toluenesulfonic acid and aqueous ethanol heated to reflux for 25 hours gave 1,4,7,10-tetra(phenylethyl)-1,4,7,10-tetraazacyclododecane (U.S. Pat. No. 4,093,615).

On the other hand, the process for the cyclotetramerization of a suitably substituted N-benzylaziridine used for the preparation of [2S-(2R*,5R*,8R*,11R*)]-2,5,8,11-tetra[(phenylmethoxy)methyl]-1,4,7,10-tetra(phenylmethyl)-1,4,7,10-tetraazacyclododecane, an intermediate for the synthesis of the ligand described in example 4 of the present application, comprises a preliminary photochemical activation which unexpectedly provides a highly sterically hindered compound (Compound (5), Scheme 4). As far as the Applicant knows, this is the first example of cyclotetramerization of an N-benzyl-aziridine substituted with a hindered functionalized group (benzyloxymethyl) at one of the two ring carbon atoms.

Furthermore, and as much unexpectedly, all of the four asymmetric carbon atoms of the macrocyclic ring of the debenzylated compound (THM-Cyclen) have the same stereochemical configuration, as described in greater detail in the experimental section (Example 4E); therefore, the configuration of the stereogenic centre of the starting aziridine has been completely retained.

The gadolinium complexes the ligand described in example 4 (2,5,8,11-tetra(hydroxymethyl)-1,4,7,10-tetraazacyclododecane-1,4,7,10-tetraacetic acid (THM-DOTA)), in its four isomeric forms RRRR, RRRS, RRSS and RSRS, were the object of a recent article of molecular modelling, concerning theoretical calculations of molecular mechanics and molecular dynamic simulations (Eur. J. Med. Chem., 30, 539–546, 1995). This article deals with purely theoretical calculations: said compounds have never been synthesized actually. Thus, the compound is novel and its preparation is particularly original, both for its applicability and the possibility of obtaining compounds with controlled stereochemistry, although highly sterically hindered.

A non-limiting list of preferred ligands of the invention (which complexes with paramagnetic ions for use as M.R.I. contrast agents are described in the Experimental section) is reported in the following, to better exemplify the wide applicative potential of the present invention.

Compound 1 (Example 1)

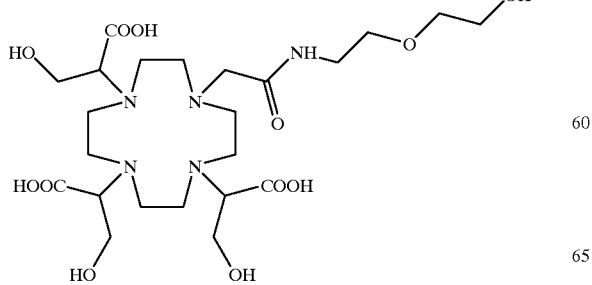

Compound 2 (Example 2)

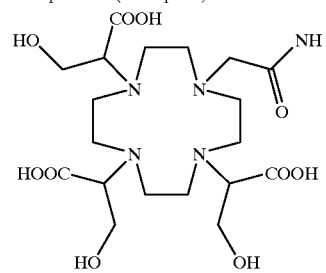

Compound 3 (Example 3)

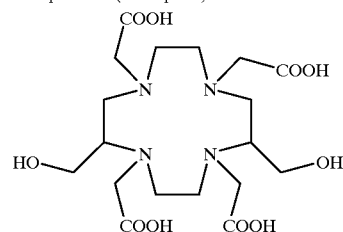

Compound 4 (Example 4)

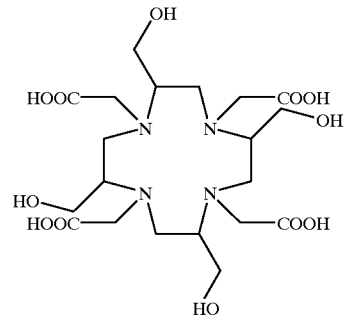

Compound 5 (Example 1)

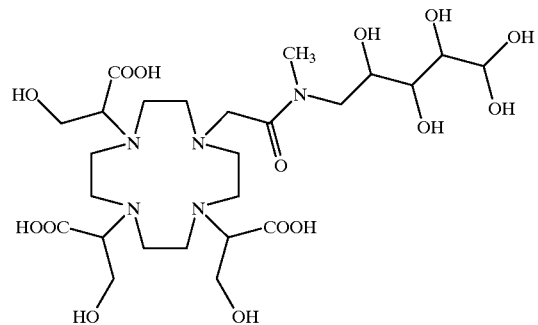

Compound 6 (Example 2)

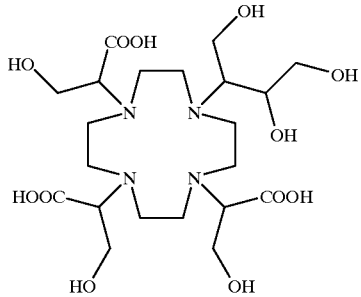

-continued

Compound 7 (Example 4)

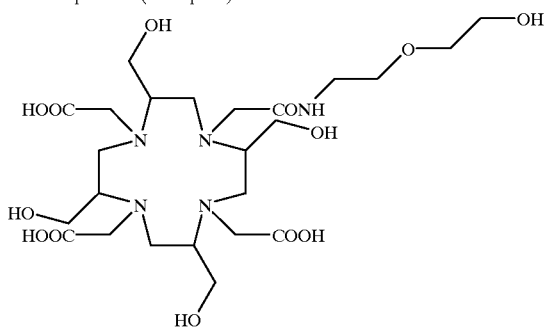

Compound 8 (Example 4)

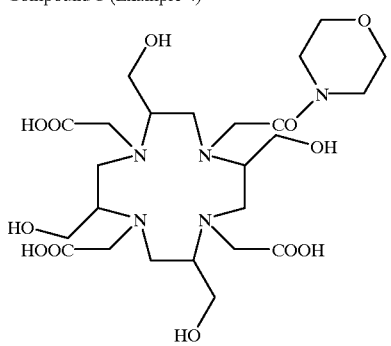

The following examples illustrate the best experimental conditions determined by the Applicant to obtain the compounds of the invention.

EXAMPLE 1

Gadolinium complex of 10-[2-[[2-(2-hydroxyethoxy)ethyl]amino]-2-oxoethyl]-α,α',α''-tris(hydroxymethyl)-1,4,7,10-tetraazacyclododecane-1,4,7-triacetic acid

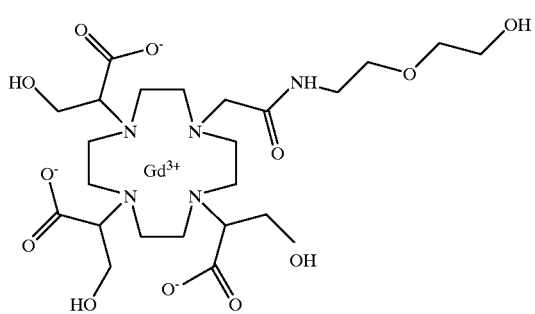

A) 2-Chloro-N-[2-(2-hydroxyethoxy)ethyl]acetamide 52.6 g of 2-(2-aminoethoxy)ethanol (commercial product) (0.5 mol) were added drop by drop to a solution of 2N HCl (20 mL; 0.04 mol), $H_2O$ (50 mL) and dioxane (50 mL) at 10÷15° C. When pH 9 was reached, a solution of chloroacetyl chloride (commercial product) (67.8 g; 0.6 mol) in dioxane (100 mL) was added. The amine and chloride solutions were added at the same time, so as to keep the pH of the mixture at 9. When the addition of amine was completed, 10N NaOH (72 mL; 0.072 mol) was added by a pH-stat so as to keep the mixture at pH 9. Dioxane was evaporated off and the residue was dissolved in $H_2O$ (400 mL); the solution was eluted on two columns of resin Duolite® A30B (700 mL) (OH⁻ form) and Duolite® C20MB (700 mL) (H⁺ form). The eluate was evaporated and the residue was purified by chromatography on silica gel:

| Stationary phase: | silica gel 230–400 mesh E. Merck cod. 9385 (150 g) |
|---|---|
| Eluent: | AcOEt (4 L) |

The desired compound was obtained (71 g; 0.39 mol). Yield 78%.
m.p.: 130–132° C. at 7 Pa
TLC: Rf 0.22

| Stationary phase: | Silica gel plates 60 F254 (E. Merck art. 5715) |
|---|---|
| Eluent: | EtOAc |
| Detection: | 1% $KMnO_4$ in 1N NaOH |

$^1$H-NMR, $^{13}$C-NMR and MS spectra are consistent with the structure.
Elemental analysis:

|  | C | H | Cl | N |
|---|---|---|---|---|
| Calc. % | 39.68 | 6.66 | 19.52 | 7.71 |
| Found % | 40.25 | 6.92 | 19.35 | 7.82 |

B) 10-[2-[[2-(2-Hydroxyethoxy)ethyl]amino]-2-oxoethyl]-α,α',α''-tris[(phenylmethoxy)methyl]-1,4,7,10-tetraazacyclododecane-1,4,7-triacetic acid 62.4 g (0.08 mol) of α,α',α''-tris[(phenylmethoxy)methyl]-1,4,7,10-tetraazacyclododecane-1,4,7-triacetic acid bis hydrochloride (obtained as described in WO 89/05802, Example 2) were dissolved in 400 ml of $H_2O$ and 8N KOH (46.2 mL; 0.37 mol). The solution was added with 58.1 g of 2-chloro-N-[2-(2-hydroxyethoxy)ethyl]acetamide (0.32 mol). The mixture was heated at 50° C. for 68 hours, keeping pH 10 by addition of 26 mL (0.21 mol) of 5N KOH by a pH-stat. The solution was acidified to pH 1.5 with 37% HCl. The precipitate was filtered, dried (50° C.; $P_2O_5$; 2 kPa) and purified by preparative HPLC:

| Stationary phase: | Lichroprep RP-8 25–40 μm; column 250 × 50 mm; |
|---|---|
| Temperature: | room temperature; |
| Mobile phase: | stepped gradient elution; A = water/acetonitrile 73:27 B = water/acetonitrile 60:40 |

| Start(min) | End(min) | % A | % B | Flow (mL min⁻¹) |
|---|---|---|---|---|
| 0 | 70 | 100 | 0 | 90 |
| 70 | 105 | 100 | 0 | 108 |
| 105 | 120 | 0 | 100 | 135 |

| Detection (UV): | 210 nm; |
|---|---|
| UV detector attenuation: | 256; |
| Injection: | 500 μL; |
| Sample concentr.: | 12 mg mL⁻¹; |
| Sample treatment: | before loading, acidify to pH 2 with HCl; |
| Instrumentation: | Merck KGaA Prepbar 100 |

The desired compound was obtained (31 g; 0.036 mol). Yield: 45%.

m.p.: 72÷75° C.
Acidic titer (0.1N NaOH): 95.6%
Complexometric titer (0.1N $ZnSO_4$): 94.7%
HPLC: 97.3% (area %)

| Stationary phase: | Spheri RP-2 10 μm; column 250 × 4.6 mm ABI; |
|---|---|
| Temperature: | 45° C.; |
| Mobile phase: | isocratic elution: A/B = 3:1 (premixed); A = 0.005M $TBAHSO_4$ in water B = $CH_3CN$ |
| Flow rate: | 1 mL min$^{-1}$; |
| Detection (UV): | 210 nm; |
| Injection: | 10 μL; |
| Sample concentr.: | 1 mg mL$^{-1}$; |
| Instrumentation: | Merck KGaA - Hitachi (L6200 and L6000) high pressure gradient pump system, Merck KGaA - Hitachi AS 2000 autosampler, Merck KGaA T 6300 column thermostat, VIS Merck KGaA - Hitachi L 4250 UV detector. |

K.F.: 0.74%
$^1$H-NMR, $^{13}$C-NMR and MS spectra are consistent with the structure.
Elemental analysis:

|  | C | H | N |
|---|---|---|---|
| Calc. % | 62.03 | 7.22 | 8.22 |
| Found % | 62.37 | 7.45 | 8.21 on anhydrous |

C) 10-[2-[[2-(2-Hydroxyethoxy)ethyl]amino]-2-oxoethyl]-α,α',α"-tris(hydroxymethyl)-1,4,7,10-tetraazacyclododecane-1,4,7-triacetic acid A solution of the compound obtained at the previous step (87.6 g; 0.103 mol) in MeOH/$H_2O$ 7:3 (v/v) (430 mL), was added with 87.6 g of 5% Pd/C; the resulting suspension was hydrogenated (hydrogen theoretical amount: 7.54 L) under 100 bar (10$^7$ Pa) and at 60–65° C. for 10 h. The mixture was cooled and the catalyst was filtered off. The filtrate was concentrated under reduced pressure to a volume of 150 mL and loaded onto an Amberlite® XAD 1600 column (1050 mL). The resin was washed with $H_2O$ until complete elution of the compound. The fractions containing the compound were combined and freeze-dried. Upon further drying (40° C.; $P_2O_5$; 2kPa), the desired compound was obtained (40.75 g; 0.07 mol).
Yield: 68%.
m.p.: 145–150° C.
Acidic titer (NaOH): 96%
Complexometric titer (0.1N $ZnSO_4$): 96%
TLC: Rf=0.7
Stationary phase: RP-8 $F_{254s}$ plates (Merck KGaA art. 15424)
Mobile phase: 0.09M $H_3PO_4$
Detection: 1% $KMnO_4$ in 1N NaOH
HPLC: 81% (area %)—Method L/303
Stationary phase: LiChrospher 100 RP-8 5 μm; 250×4 mm Merck KGaA column;
Temperature: 40° C.;
Mobile phase: isocratic elution with premixed mobile phase: 1 g of n-octylamine is added to 50 ml of acetonitrile mixed with 950 ml of water. The solution is buffered to pH 6 with $H_3PO_4$;
Flow rate: 1 mL min$^{-1}$;
Detection (UV): 210 nm;
Injection: 10 μL;
Sample concentr.: 1–5 mg mL$^{-1}$;
Instrumentation: Merck KGaA—Hitachi L6000 low pressure gradient pump system, Merck KGaA—Hitachi AS 2000 autosampler, Merck KGaA T 6300 column thermostat, Merck KGaA—Hitachi L 3000 developer.
K.F.: 2.62%
$^1$H-NMR, $^{13}$C-NMR and MS spectra are consistent with the structure.
Elemental analysis:

|  | C | H | N |  |
|---|---|---|---|---|
| Calc. % | 47.50 | 7.45 | 12.04 |  |
| Found % | 46.60 | 7.67 | 12.10 | sulthe anhydrous |

D) Gadolinium complex of 10-[2-[[2-(2-hydroxyethoxy)ethyl]amino]-2-oxoethyl]-α,α', α"-tris(hydroxymethyl)-1,4,7,10-tetraazacyclododecane-1,4,7-triacetic acid A solution of the compound obtained at the previous step (30.29 g; 0.050 mol) in $H_2O$ (300 mL), was added with $Gd_2O_3$ (9.06 g; 0.025 mol) and the resulting suspension was stirred at r.t. for 65 h. The insoluble residue was filtered off through Millipore HA 0.45 μm and the filtrate was concentrated to 100 mL under reduced pressure, then loaded onto an Amberlite® XAD 1600 column (1700 mL). The resin was washed with $H_2O$ (9 L), $H_2O$/$CH_3CN$ 95:5 (v/v) (2 L), $H_2O$/$CH_3CN$ 90:10 (v/v) (2.5 L). The fractions containing the compound were combined, concentrated under reduced pressure and freeze-dried to obtain 36.15 g of compound.

A portion (19 g) was further purified by reversed phase preparative chromatography:

| Stationary phase: | LiChroprep® RP-8 40–63 μm; 200 g; |
|---|---|
| Column: | 600 × 26 mm Superformance® Merck KGaA; |
| Temperature: | r.t.; |
| Mobile phase: | $H_2O$; |
| Flow rate: | 3 mL min$^{-1}$; |
| Detection: | Spectrophotometric (UV) 206 nm; Conductimetric; |
| Injection: | 4 mL; |
| Sample concentr.: | 0.5 g mL$^{-1}$; |
| Instrumentation: | Merck KGaA - Hitachi L6000 low pressure gradient pump system, Pharmacia LKB UVICORD S II UV detector, Metrohm 660 conductimeter fitted with CLR cell Mod. 401/D Series 9302 |

The fractions containing the pure compound were combined, concentrated under reduced pressure and freeze-dried. After further drying ($P_2O_5$; 2 kPa), the desired compound was obtained (15.3 g; 0.0208 mol).
Yield: 79%
m.p.: >250° C.
Free ligand (HPLC): <0.01% (Method L/303, Example 1C)
TLC: Rf 0.42

| Stationary phase: | plates RP-8 $F_{254s}$ (Merck KGaA art. 15424) |
|---|---|
| Eluent: | $H_2O$ |

-continued

| | | |
|---|---|---|
| Detection: | 1% KMnO₄ in 1N NaOH | |
| HPLC: | 99.5% (area %) (Method L/303, Example 1C) | |
| K.F.: | 3.62% | |

The mass spectrum is consistent with the structure.
Elemental analysis:

| | C | H | Gd | N | |
|---|---|---|---|---|---|
| Calc. % | 37.54 | 5.48 | 21.36 | 9.51 | |
| Found % | 37.40 | 5.70 | 21.16 | 9.51 | on anhydrous |

The following compounds were obtained analogously:

Dysprosium complex of 10-[2-[[2-(2-hydroxyethoxy)ethyl]amino]-2-oxoethyl]-α,α',α"-tris(hydroxymethyl)-1,4,7,10-tetraazacyclododecane-1,4,7-triacetic acid Gadolinium complex of 1-deoxy-1-[methyl[1-oxo-2-[4,7,10-tris(1-carboxy-2-hydroxyeth-1-yl)-1,4,7,10-tetraazacyclododec-1-yl]ethyl]amino]-D-glucitol Dysprosium complex of 1-deoxy-1-[methyl[1-oxo-2-[4,7,10-tris(1-carboxy-2-hydroxyeth-1-yl)-1,4,7,10-tetraazacyclododec-1-yl]ethyl]amino]-D-glucitol.

EXAMPLE 2

Gadolinium complex of α,α',α"-Tris(hydroxymethyl)-10-(2-hydroxypropyl)-1,4,7,10-tetraazacyclododecane-1,4,7-triacetic acid

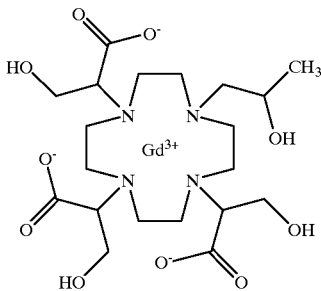

A) 10-(2-Hydroxypropyl)-α,α',α"-tris[(phenylmethoxy)methyl]-1,4,7,10-tetraazacyclododecane-1,4,7-triacetic acid bis hydrochloride.

4.7 g (0.08 mol) of propylene oxide were added drop by drop, in 15 minutes, to a solution of α,α'α"-tris[(phenylmethoxy)methyl]-1,4,7,10-tetraazacyclododecane-1,4,7-triacetic acid bis hydrochloride (obtained as described in WO 89/05802, Example 2) (31.2 g; 0.04 mol) in 2N KOH (160 mL; 0.32 mol). After 18 hours at room temperature (20° C.), the reaction mixture was diluted with H₂O (250 mL). The solution was acidified with 37% HCl (60 mL), to obtain a precipitate which, after 18 hours, was filtered, washed with 2N HCl (50 mL) and dried (P₂O₅—NaOH; 50° C.; 2 kPa) to obtain the desired compound (31.7 g dry; 0.037 mol).

Yield: 92%.

m.p.: 165° C. (synt.) 171° C. (dec.)

Acidic titer (0.1N NaOH): 100.2%

Argentometric titer (0.1N AgNO₃): 98%

HPLC: 97% (area%)—Method L/247

| | |
|---|---|
| Stationary phase: | Column E. Merck Lichrosorb RP-2; 5 μm; 250 × 5 mm |
| Mobile phase: | Isocratic elution A/B 4:1 A = 0.005M TBAHSO₄ in water B = CH₃CN |
| Flow: | 2 mL min⁻¹ |
| Temperature: | 45° C. |
| Injection: | 10 μL |
| Sample concentr.: | 1 mg mL⁻¹ |
| Detection: | UV 210 nm |
| K.F.: | 2.75% |

¹³C-NMR and MS spectra are consistent with the structure.

Elemental analysis:

| | C | H | N | Cl⁻ | |
|---|---|---|---|---|---|
| Calc. % | 58.78 | 6.98 | 6.69 | 8.46 | |
| Found % | 58.16 | 6.96 | 6.52 | 8.22 | on anhydrous |

B) α,α',α"-tris(hydroxymethyl)-10-(2-hydroxypropyl)-1,4,7,10-tetraazacyclododecane-1,4,7-triacetic acid A solution of the compound obtained at the previous step (83.8 g; 0.0985 mol) in MeOH/H₂O 2:1 (v/v) (300 mL), adjusted to pH 7.5 with 10N NaOH (40 mL; 0.4 mol), was added with 5% Pd/C (84 g) and the resulting suspension was hydrogenated in a Parr bomb (mod. 4561, 600 mL) (hydrogen theoretical amount 6.6 L; 0.295 mol), under 10⁷ Pa (100 bar) and at 75–80° C. for 24 h. The mixture was cooled, filtered by suction and then through Millipore® HA 0.45 μm. The filtrate was concentrated to 250 mL under reduced pressure and, after adjusting to pH 4 with 2N HCl (180 mL; 0.36 mol), was loaded onto an Amberlite® XAD 1600 column (1.8 L). The resin was eluted with H₂O, the fractions containing the ligand were combined and the compound was freeze-dried, to obtain the desired compound salified with 0.23 HCl molar equivalents.

Yield: 58%.

m.p.: 130–135° C.

Acidic titer (0.1N NaOH): 124.5%; equivalent point at pH 6.03

Complexometric titer (0.1N ZnSO₄): 97%

TLC: Two spots at $R_f$ 0.65 and $R_f$ 0.7 Stationary phase: plates RP-8 $F_{254s}$ (Merck KGaA art. 15424)

Eluent: H₂O

Detection: 1% KMnO₄ in 1N NaOH

Note: The compound consists of a couple of diastereomers, each being a racemic mixture.

HPLC: 99.9% (area %)—Method L/324

| | |
|---|---|
| Stationary phase: | Lichrosorb RP-2 5 μm; column 250 × 4 mm Alltech; |
| Temperature: | 45° C.; |
| Mobile phase: | isocratic elution: 0.005M tetrabutylammonium hydrogen sulfate; |
| Flow rate: | 1 mL min⁻¹; |
| Detection (UV): | 210 nm; |
| Injection: | 10 μL; |
| Sample concentr.: | 5–10 mg mL⁻¹; |

-continued

| Instrumentation: | Merck KGaA - Hitachi L6000 low pressure gradient pump system, Merck KGaA - Hitachi AS 2000 autosampler, Merck KGaA T 6300 column thermostat, Merck KGaA - Hitachi L 3000 diode array detector. |

K.F.: 2.86%

$^1$H-NMR, $^{13}$C-NMR and MS spectra are consistent with the structure.

Elemental analysis:

|  | C | H | N | Cl$^-$ |
|---|---|---|---|---|
| Calc. % | 47.76 | 7.66 | 11.14 | 1.62 |
| Found % | 48.15 | 7.82 | 11.13 | 1.78 on anhydrous |

C) Gadolinium complex of α,α'α"-tris(hydroxymethyl)-10-(2-hydroxypropyl)-1,4,7,10-tetraazacyclododecane-1,4,7-triacetic acid A solution of the compound obtained at the previous step (32.85 g; 0.05 mol) in H$_2$O (300 mL) was added with Gd$_2$O$_3$ (9.06 g; 0.025 mol) and the resulting suspension was stirred at r.t. for 66 hours. The pH of the solution was adjusted to 6.5 with 1N HCl (7.5 mL; 7.5 mmol) and the insoluble residue was filtered off through Millipore HA 0.45 μm. The filtrate was concentrated under reduced pressure to 250 mL (bath temperature 30° C.) and then electrodyalised for 25 hours:

Apparatus: HAR ED 0.004 (Hydro Air Research);

Electrode solution: 2% Na$_2$SO$_4$ (w/v) buffered at pH 3 with 1M H$_2$SO$_4$; 0.2% NaCl (w/v);

Voltage: 12 V

The retentate was concentrated under reduced pressure to 100 mL (bath temperature ~30° C.) and then loaded onto a Relite® column 3AS/FB (170 mL; HCO$_3$$^-$ form) followed by a Dowex® CCR-3 LB column (170 mL; H$^+$ form). The resin was washed with H$_2$O until all the compound was eluted (4 L) (flow: 5 mL/min). After drying (P$_2$O$_5$; 2 kPa), the desired compound was obtained (28.4 g; 0.044 mol).

Yield: 88%.

m.p.: >250° C.

Free ligand: 0.01% (HPLC) (method L/303, Example 1C); 0.01% (complexometric titration)

TLC: Rf 0.32

TLC: plates RP-8 F$_{254s}$ (Merck KGaA art. 15424)

Eluent: H$_2$O

Detection: 1% KMnO$_4$ in 1N NaOH

HPLC: two peaks at Rt 3.64 min (56%) and Rt 3.85 min (44%) (area %)

Method: L/303, Example 1C

Injection: 20 μL;

Sample concentr.: 10 mg mL$^{-1}$;

K.F.: 4.33%

The mass spectrum is consistent with the structure.

Elemental analysis:

|  | C | H | Gd | N |
|---|---|---|---|---|
| Calc. % | 37.02 | 5.43 | 24.23 | 8.63 |
| Found % | 37.10 | 5.60 | 23.88 | 8.49 on anhydrous |

The following compounds were obtained analogously:

Dysprosium complex of α,α',α"-tris(hydroxymethyl)-10-(2-hydroxypropyl)-1,4,7,10-tetraazacyclododecane-1,4,7-triacetic acid Gadolinium complex of α,α',α"-tris(hydroxymethyl)-10-[2,3-dihydroxy-1-(hydroxymethyl)propyl]-1,4,7,10-tetraazacyclododecane-1,4,7-triacetic acid Dysprosium complex of α,α',α"-tris(hydroxymethyl)-10-[2,3-dihydroxy-1-(hydroxymethyl)propyl]-1,4,7,10-tetraazacyclododecane-1,4,7-triacetic acid.

EXAMPLE 3

Gadolinium complex of 2,9-bis(hydroxymethyl)-1,4,7,10-tetraazacyclododecane-1,4,7,10-tetraacetic acid salified with 1-deoxy-1-(methylamino)-D-glucitol (1:1)

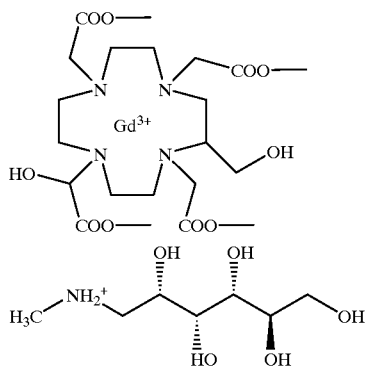

A) 3-Benzyloxy-2-chloropropionic acid

The compound was prepared as reported in WO 89/05802.

B) 3-Benzyloxy-2-chloropropionyl chloride 250 g of thionyl chloride (2.1 mol) were added drop by drop to 107.3 g of acid obtained at the previous step (0.5 mol), keeping the mixture at 30° C. by heating. At the end of the addition, the resulting solution was refluxed for two hours (65–80° C.). The thionyl chloride excess was distilled off (15 mbar), then the desired compound (110 g; 0.472 mol) was distilled (0.05 mbar) from the residue.

Yield: 94.4%.

b.p.: 119–120° C. (0.2 mbar)

Argentometric titer (after Zn reduction): 98.7%

Argentometric titer (after NaOH hydrolysis): 100.7%

Elemental analysis:

|  | C | H | Cl |
|---|---|---|---|
| Calc. % | 51.53 | 4.32 | 30.42 |
| Found % | 51.46 | 4.37 | 29.50 |

$^1$H-NMR, $^{13}$C-NMR and IR spectra are consistent with the structure.

C) N,N'-ethylenebis[2-iodo-3-(phenylmethoxy)-N-(phenylmethyl)propanamide]

A solution of 2-chloro-3-benzyloxypropionyl chloride (140 g; 0.6 mol) and $K_2CO_3$ (91.2 g; 0.66 mol) in $CHCl_3$/$H_2O$ (1:1) (1000 mL) at −5° C. was slowly added, in an hour, with 48.1 g of N,N'-dibenzylethylenediamine (0.2 mol). After 1 hour at 0° C., the mixture was stirred for a further 4 hours at room temperature. The phases were partitioned, the organic phase was washed with $H_2O$ (500 mL), dried over $Na_2SO_4$ and evaporated to dryness. The crude was purified by flash chromatography (silica gel; n-hexane/ethyl acetate, 8:2 v/v). The resulting oil was dissolved in acetone (500 mL), then NaI (60 g; 0.4 mol) was added. The solution was refluxed for 30 hours. After cooling at 5° C., the mixture was filtered and the solvent evaporated off under reduced pressure. The oil was dissolved in $CH_2Cl_2$ (300 mL) and washed with $H_2O$ (300 mL). The phases were partitioned, the organic phase was dried over $Na_2SO_4$ and evaporated to dryness, to obtain the desired compound (157 g; 0.19 mol).

Yield: 96%.

HPLC titre: 96.4% (area)—Method L 241

| Stationary phase: | E. Merck Lichrospher 100 RP-18 5 μm; column 250 × 4 mm E. Merck; |
|---|---|
| Mobile phase: | gradient elution; A = 0.01M $KH_2PO_4$ and 0.017M $H_3PO_4$ in water B = $CH_3CN$; |
| Gradient timetable: | min   % A   % B<br>0      95     5<br>20     20    80<br>45     20    80 |
| Flow rate: | 1 mL min$^{-1}$; |
| Temperature: | 45° C.; |
| Injection: | 10 μL; |
| Sample concentr.: | 1 mg mL$^{-1}$; |
| Detection (UV): | 210 nm. |

$^1$H-NMR, $^{13}$C-NMR, MS and IR spectra are consistent with the structure.

D) 3,8-Bis[(phenylmethoxy)methyl]-1,4,7,10-tetra(phenylmethyl)-1,4,7,10-tetraazacyclododecane-2,9-dione A suspension of the compound obtained at the previous step (200 g; 0.24 mol) and $Na_2CO_3$ (424 g; 4.0 mol) in $CH_3CN$ (5000 mL) was added, at r.t., with N,N'-dibenzylethylenediamine (58.9 g; 0.24 mol). The reaction was stirred at 81° C. under inert atmosphere for 16 days, monitoring its progress by HPLC (method L 241, Example 3C). After cooling at 5° C., the solid was filtered off and the solution evaporated to dryness. The oily residue was dissolved in $CH_2Cl_2$ (500 mL) and washed with $H_2O$ (500 mL); the organic phase was dried over $Na_2SO_4$ and evaporated, thereby obtaining a crude (200 g) which was purified by flash chromatography (silica gel; n-hexane/ethyl acetate, 9:1 v/v). The solvent was evaporated off and the solid residue (61 g) was recrystallized from 2-propanol (200 mL), to obtain the desired compound (56 g; 0.07 mol).

Yield: 29%.

HPLC titre: 100% (area)—Method L 241, Example 3C m.p.: 86–87° C.

$^1$H-NMR, $^{13}$C-NMR, MS and IR spectra are consistent with the structure.

K.F.: <0.1%

Elemental analysis:

|  | C | H | N |
|---|---|---|---|
| Calc. % | 77.97 | 7.05 | 6.99 |
| Found % | 77.94 | 7.06 | 6.96 |

E) 2,9-Bis[(phenylmethoxy)methyl]-1,4,7,10-tetra(phenylmethyl)-1,4,7,10-tetraazacyclododecane A solution of the compound obtained at the previous step (37 g; 46.2 mmol) in toluene (300 mL) kept at 5° C. under inert atmosphere was added, in 30 min., with a solution of sodium bis(2-methoxyethoxy)aluminium hydride (RED-Al®) in toluene (100 mL; 0.35 mol). The reaction mixture was heated at 80° C. for 1 hour. After cooling at −15° C., the RED-Al® excess was carefully destroyed by addition of $H_2O$ (25 mL) to the reaction mixture. After 2 hours at 0° C., the colloid was filtered through a G3 septum filled with a two-layer bed of sand (top) and silica gel (230–400 mesh) (bottom). The organic phase was dried over $Na_2SO_4$ and evaporated to dryness, to obtain the desired compound (32 g; 41.4 mmol).

Yield: 90%.

HPLC titre: 98.2% (area)

| Stationary phase: | E. Merck Lichrosorb RP-Select-B 5 μm; column 250 × 4 mm E. Merck; |
|---|---|
| Temperature: | 45° C.; |
| Mobile phase: | gradient elution; A = 0.01M $KH_2PO_4$ and 0.017M $H_3PO_4$ in water B = $CH_3CN$ |
| Gradient timetable: | min   % A   % B<br>0      95     5<br>30     20    80<br>45     20    80 |
| Flow rate: | 1 mL min$^{-1}$; |
| Detection (UV): | 210 nm, 280 nm; |
| Injection: | 10 μL; |
| Sample concentr.: | 1 mg mL$^{-1}$; |
| Instrumentation: | E. Merck - Hitachi (L6200 and L6000) high pressure gradient pump system, E. Merck - Hitachi AS 2000 autosampler, E. Merck T 6300 column thermostat, E. Merck - Hitachi L 4250 UV detector. |

$^1$H-NMR, $^{13}$C-NMR, MS and IR spectra are consistent with the structure.

F) 2,9-Bis(hydroxymethyl)-1,4,7,10-tetraazacyclododecane

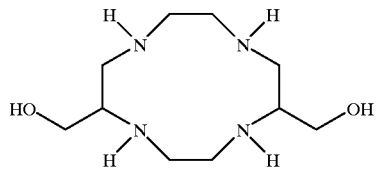

A solution of the compound obtained at the previous step (12.3 g; 15.9 mmol) in EtOH/toluene (10:1; v/v) (400 mL) was added with 12 g of 20% Pd(OH)$_2$/C. The mixture was hydrogenated at 35° C. and under atmosphere pressure for 24 hours. The catalyst was filtered off through a paper filter and washed with $H_2O$/EtOH (1:1; v/v) (200 mL). The solvent was evaporated off, the crude was dissolved in $H_2O$ (20 mL) and percolated on an IRA 400 ion exchange resin column (200 mL; OH⁻ form). The solvent was evaporated off to obtain the desired compound (3.1 g; 13.3 mmol).

Yield: 84%.

HPLC titre: 100% (area)—Method L/270 B

| Stationary phase: | E. Merck Superspher RP-18 endcapped; column 250 × 4 mm Lichrocart E. Merck; |
|---|---|
| Temperature: | 40° C.; |
| Mobile phase: | isocratic elution: A = 0.005M tetrabutylammonium hydrogen sulfate in water; |
| Flow rate: | 1 mL min⁻¹; |
| Detection (UV): | 210; 280 nm; |
| Injection: | 10 μL; |
| Sample preparat.: | dissolve 10 mg of the substance to analyze in 1 mL of a 0.1M CuSO₄ solution, then dilute to 10 mL with the eluent; |
| Instrumentation: | E. Merck - Hitachi L 6200 low pressure gradient pump system, E. Merck - Hitachi AS 2000 autosampler, E. Merck T6300 column thermostat, E. Merck - Hitachi L 4000 UV detector, E. Merck - Hitachi L 3000 diode array detector. | m.p.: 175–176° C.

¹H-NMR, ¹³C-NMR, MS and IR spectra are consistent with the structure.

G) Gadolinium complex of 2,9-bis(hydroxymethyl)-1,4,7,10-tetraazacyclododecane-1,4,7,10-tetraacetic acid salified with 1-deoxy-1-(methylamino)-D-glucitol (1:1)

A solution of the compound obtained at the previous step (3.5 g; 0.015 mol) in H₂O (25 mL) was added with bromoacetic acid (8.34 g; 0.06 mol) in H₂O (25 mL), then adjusted to pH 10 with 6N NaOH (12 mL). The reaction mixture was stirred at 40° C., keeping the pH at 10 with 2N NaOH. After 24 hours, bromoacetic acid (8.34 g; 0.06 mol) was added and the solution was stirred at 40° C. and pH 10 for a further 24 hours. After cooling at 20° C., the reaction mixture was concentrated (20 mL) and pH adjusted to 3.5 with 6N HCl. The solution was loaded onto an Amberlite® C 20 MB column (H⁺ form; 600 mL), eluted with H₂O to neutrality and then with 2N NH₄OH until complete elution of the compound. The solution was concentrated to 20 mL, then acidified to pH 1.5 with 6N HCl, loaded onto a column of Duolite® XAD 1600 resin (1200 mL) and eluted with H₂O. After concentration to 10 mL, EtOH (100 mL) was added; the resulting precipitate was filtered and washed with EtOH (20 mL), to obtain the ligand, 2,9-bis(hydroxymethyl)-1,4,7,10-tetraazacyclododecane-1,4,7,10-tetraacetic acid (3.91 g; 6.9 mmol).

HPLC titre: 100% (area %)—Method L/270 B, Example 3F

NMR and MS spectra are consistent with the structure.

A solution of the ligand (3.91 g; 6.9 mmol) in H₂O (25 mL) was slowly added with GdCl₃×6 H₂O (2.56 g; 6.9 mmol) keeping pH 7 by addition of 1-deoxy-1-(methylamino)-D-glucitol (5.39 g; 27.6 mmol) in H₂O (30 mL). The solution was stirred for 48 hours at r.t. and filtered through Millipore® (HA-0.22 μm). The solution was concentrated and the residue purified on Amberlite® XAD 1600 resin (1200 mL). The solvent was evaporated off to obtain the gadolinium complex of 2,9-bis(hydroxymethyl)-1,4,7,10-tetraazacyclododecane-1,4,7,10-tetraacetic acid salified with 1-deoxy-1-(methylamino)-D-glucitol (1:1) (3.0 g; 3.69 mmol).

Yield: 25%.
m.p.: >250° C. (dec.)
Free ligand (0.001 M GdCl₃): <0.1%
HPLC titre: 99.8% (area %)

| Stationary phase: | E. Merck Lichrospher 100 RP-18 5 μm; column 250 × 4 mm E. Merck; |
|---|---|
| Temperature: | 40° C.; |
| Mobile phase: | isocratic elution with premixed mobile phase: 1 g of n-octylamine is added to 200 ml of acetonitrile mixed with 800 ml of water. The solution is buffered to pH 6 with H₃PO₄; |
| Flow rate: | 1 mL min⁻¹; |
| Detection (UV): | 210 nm; |
| (FL): | ex = 275 nm; em = 310 nm; |
| Injection: | 10 μL; |
| Sample concentr.: | 1 mg mL⁻¹; |
| Instrumentation: | E. Merck - Hitachi (L6200 and L6000) high pressure gradient pump system, E. Merck - Hitachi AS 2000 autosampler, E. Merck T 6300 column thermostat, E. Merck - Hitachi L 4250 UV detector, E. Merck - Hitachi F 1080 fluorescence detector. |

MS and IR spectra are consistent with the structure.
K.F.: 9.71%
Elemental analysis:

|  | C | H | N | Gd |
|---|---|---|---|---|
| Calc. % | 36.89 | 5.70 | 8.60 | 19.32 |
| Found % | 35.74 | 5.28 | 8.60 | 20.70 on anhydrous |

The dysprosium complex of 2,9-bis(hydroxymethyl)-1,4,7,10-tetraazacyclododecane-1,4,7,10-tetraacetic acid salified with 1-deoxy-1-(methylamino)-D-glucitol (1:1) was obtained analogously.

EXAMPLE 4

Gadolinium complex of [2S-(2R*,5R*,8R*,11R*)]-2,5,8,11-tetra(hydroxymethyl)-1,4,7,10-tetraazacyclododecane-1,4,7,10-tetraacetic acid sodium salt (1:1) (Na⁺Gd[THM-DOTA]⁻)

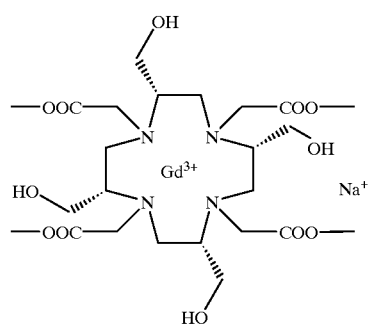

A) (R)-2-Amino-3-(phenylmethoxy)propanol

A mixture of O-(phenylmethyl)-L-serine (commercial product) (139.0 g; 0.712 mol) and NaBH₄ (96%; 75 g; 1.9 mol) in dry THF (700 mL, distilled on sodium/benzophenone), under N₂ atmosphere, was slowly added (1.5 hours) with a solution of I2 (181.0 g; 0.713 mol) in dry THF (350 mL) at a temperature of 0 to 15° C. When the addition was completed and the dark color had disappeared, the mixture was refluxed for 18 hours, then cooled at 0° C. and the NaBH$_4$ excess was destroyed with cold water (30 mL), followed by 15N KOH (320 mL). When bubble evolution was no longer observed, the mixture was heated, distilling most of the organic solvent (THF). The aqueous mixture was refluxed for 6 hours, then stirred at r.t. for a further 18 hours. CHCl$_3$ (700 mL) and Et$_2$O (300 mL) were added thereto under strong stirring; after 15 minutes the diphasic mixture was filtered through Celite® and the separated solid was repeatedly washed with CHCl$_3$/Et$_2$O 3:1 (4 L). The filtered solution was concentrated, removing water by repeated azeotropical distillations with CH$_3$CN. The crude oil (130 g) was purified twice by flash chromatography (CH$_2$Cl$_2$/CH$_3$OH/NH$_4$OH 25% (w/w) 54:40:6 to 90:9:1), thereby obtaining the desired compound (92.63 g; 0.511 mol).

Yield: 72%.
TLC: R$_f$ 0.57

| | | |
|---|---|---|
| Stationary phase: | silica gel. | |
| Eluent: | CH$_2$Cl$_2$/CH$_3$OH/25% NH$_4$OH (w/w) (v/v). | 82:15:3 |
| Detection: | 254 nm; 0.5% KMnO$_4$ in 1N NaOH; | 0.2% |
| | ninhydrin(w/v) in EtOH; | 2% |
| | Ce(SO$_4$)$_2$.4H$_2$O (w/v), | 4.2% |
| | (NH$_4$)$_6$Mo$_7$O$_{24}$ (w/v), 6% H$_2$SO$_4$ (w/v) in water. | |
| HPLC titre: | 98% (area) - Method L/242 B | |
| Stationary phase: | Lichrosorb RP-Select B 5 µm; column 250 x 4 mm Merck KGaA; | |
| Temperature: | 50° C.; | |
| Mobile phase: | gradient elution; A = 0.01M KH$_2$PO$_4$ in water B = CH$_3$CN | |
| Gradient timetable: | min %A %B | |
| | 0 90 10 | |
| | 10 90 10 | |
| | 30 30 70 | |
| Flow rate: | 1 mL min$^{-1}$; | |
| Detection (UV): | 220 nm; | |
| Injection: | 10 µL; | |
| Sample concentr.: | 2 mg mL$^{-1}$; | |
| Instrumentation: | Merck KGaA - Hitachi L 6200 low pressure gradient pump system, Merck KGaA - Hitachi AS 2000 autosampler, Merck KGaA T6300 column thermostat, Merck KGaA - Hitachi L 4000 UV detector. | |

$^1$H-NMR, $^{13}$C-NMR, MS and IR spectra are consistent with the structure.

Rotatory power:
[α]$_{589}^{20}$=+5, 0°;
[α]$_{579.07}^{20}$=+5, 2°;
[α]$_{576.96}^{20}$=+5, 3°;
[α]$_{546.07}^{20}$=+5, 6°;
[α]$_{435.83}^{20}$=+9, 7°;
[α]$_{407.78}^{20}$=+11, 5°(c 1, 85; THF).

B) (R)-3-(Phenylmethoxy)-2-[(phenylmethyl)amino]propanol

A solution of aminoalcohol obtained at the previous step (201.7 g; 1.113 mol) in dry THF (4 L, distilled on sodium/benzophenone) under N$_2$ atmosphere, was added with benzaldehyde (purified by distillation under reduced pressure: 120 mL; 1.19 mol), anhydrous MgSO$_4$ (120 g) and 4 Å molecular sieves (dried in oven under vacuum, 70° C.); the mixture was stirred for 2 hours, then filtered and the solvent was evaporated off; the residual oil was dissolved in absolute ethanol (4 L), the reaction mixture was cooled on ice bath, then added with NaBH$_4$ (96%; 40.35 g; 1.02 mol) in small portions. After 20 hours, the excess of reducing agent was carefully destroyed with 20% HCl (w/v) (800 mL). Most ethanol was evaporated off in rotary evaporator; solid KOH and subsequently Na$_2$CO$_3$ were added to pH about 10. The aqueous mixture was extracted with CH$_2$Cl$_2$. The combined organic phases were concentrated under vacuum and subjected to repeated azeotropical distillations with CH$_3$CN, thereby obtaining the desired compound (296.7 g; 1.093 mol).

Yield: 98%.
TLC: R$_f$ =0.45

| | | |
|---|---|---|
| Stationary phase: | silica gel | |
| Eluent: | C$_6$H$_5$CH$_3$/CH$_3$COOEt/i-PrOH (v/v) | 50:45:5 |
| Detection: | 254 nm; 0.5% KMnO$_4$ in 1N NaOH; ninhydrin(w/v) in EtOH; | 0.2% |
| HPLC: | 85% (area) - Method L/153 A | |
| Stationary phase: | Lichrosorb RP-Select B 5 µm; column 250 x 4 mm Merck KGaA; | |
| Temperature: | 40° C.; | |
| Mobile phase: | gradient elution; A = 0.017M KH$_2$PO$_4$ in water B = CH$_3$CN | |
| Gradient timetable: | min %A %B | |
| | 0 90 10 | |
| | 5 90 10 | |
| | 30 20 80 | |
| | 50 20 80 | |
| Flow rate: | 1 mL min$^{-1}$; | |
| Detection (UV): | 210 nm; | |
| Injection: | 10 µL; | |
| Sample concentr.: | 1 mg mL$^{-1}$; | |
| Instrumentation: | Merck KGaA - Hitachi (L6200) high pressure gradient pump system, Merck KGaA - Hitachi AS 2000 autosampler, Merck KGaA T 6300 column thermostat, Merck KGaA - Hitachi L 4250 UV detector. | |

$^1$H-NMR, $^{13}$C-NMR, MS and IR spectra are consistent with the structure.

C) (R)-2-[(Phenylmethoxy)methyl]-1-(phenylmethyl)aziridine

A solution of the N-benzyl-aminoalcohol obtained at the previous step (47.34 g; 0.175 mol), and PPh$_3$ (50.86 g; 0.194 mol) in dry THF (800 mL; distilled on sodium/benzophenone) cooled on ice bath, under N$_2$ atmosphere, was added with diisopropyl azodicarboxylate (product Fluka art. 11626) (39.5 mL; 0.18–0.20 mol) during 2 hours with a syringe pump. The reaction temperature was kept at 5° C. for 16 h. The mixture was then concentrated under vacuum, the crude dissolved in n-hexane/CH$_2$Cl$_2$ 3:1 and the precipitate filtered. This procedure was carried out repeatedly to remove most Ph$_3$PO (72.85 g). The resulting crude oil was purified twice by flash chromatography (n-hexane/CH$_2$Cl$_2$/i-PrOH 55:40:5; C$_6$H$_5$CH$_3$/CH$_3$COOEt/i-PrOH 9:1:0.05 to 8:2:0.05) to obtain the desired compound (39.78 g; 0.157 mol).

Yield: 90%.
TLC: R$_f$ 0.70

| | | |
|---|---|---|
| Stationary phase: | silica gel | |
| Eluent: | C$_6$H$_5$CH$_3$/CH$_3$COOEt/i-PrOH (v/v) | 60:35:5 |
| Detection: | 254 nm; 0.5% KMnO$_4$ in 1N NaOH; Ce(SO$_4$)$_2$.4H$_2$O (w/v), (NH$_4$)$_6$Mo$_7$O$_{24}$ (w/v), 6% H$_2$O$_4$ (w/v) in water | 2% 4.2% |
| GC: | 95% (area) | |
| Stationary phase: | HP 5; | |

-continued

| | | |
|---|---|---|
| Film thickness: | 2.65 μm; | |
| Column (WCOT): | 10 m × 0.53 mm; | |

¹H-NMR, ¹³C-NMR, MS and IR spectra are consistent with the structure.
Enantiomeric purity: >99.5%
K.F.: <0.1%
Elemental analysis:

| | C | H | N |
|---|---|---|---|
| Calc. % | 80.60 | 7.56 | 5.53 |
| Found % | 80.53 | 7.75 | 6.05 |

D) [2S-(2R*,5R*,8R*,11R*)]-2,5,8,11-tetra[(phenylmethoxy)methyl]-1,4,7,10-tetra(phenylmethyl)-1,4,7,10-tetraazacyclododecane A six-necked flask was equipped with the following instrumentation: a mechanical stirrer; a 150 W high-pressure mercury-vapor lamp, inserted in a refrigerated Pyrex filter; a capillary through which dry air is bubbled into the reaction mixture; a syringe pump; a thermometer; a Graham condenser, connected with a gentle $N_2$ stream. The flask was immersed in a water bath maintained at about 50° C.

⅕ of a 4-toluenesulfonic acid solution (PTSA $H_2O$, 43.28 g; 0.228 mol) in $CH_3CN$ (400 mL) was added to a solution of the aziridine obtained at the previous step (229.13 g; GC 89%; 0.805 mol) and 9,10-dicyanoanthracene (DCA) (1.69 g; 7.40 mmol) in $CH_3CN$ (4.5 L). After 45 min, the remaining acid catalyst was added drop by drop to the reaction mixture in 6 hours, by means of the syringe pump. After 7.5 hours, heating and lighting were stopped. After 18 hours, water (0.5 L) and solid $K_2CO_3$ (40 g) were added with strong stirring. The organic solvent was evaporated off and the aqueous phase was extracted with $CHCl_3$. The combined organic phases were washed with buffer 0.1M $KH_2PO_4$/$K_2HPO_4$ at pH 7 (0.5 L), then dried over $MgSO_4$. The crude oil resulting from the evaporation of the solvent (272.5 g) was purified by flash chromatography ($CH_3Cl$/$CH_3OH$/25% $NH_4OH$ (w/w) 1000:13:3 (v/v)), thereby obtaining the desired compound (51.64 g; 51.0 mmol).
Yield: 25%.
TLC: $R_f$ = 0.50

| | |
|---|---|
| Stationary phase: | silica gel |
| Eluent: | $CH_2Cl_2$/$CH_3OH$/25% $NH_4OH$ (w/w) 1000:17:3 (v/v) |
| Detection: | 254 nm; 0.5% $KMnO_4$ in 1N NaOH. |
| HPLC: | 97% (area) - Method L/282 A |
| Stationary phase: | Lichrosorb RP-Select B 5 μm; column 250 × 4 mm Merck KGaA; |
| Temperature: | 35° C.; |
| Mobile phase: | gradient elution; A = 0.017M $H_3PO_4$ in water B = $CH_3CN$ |
| Gradient timetable: | min %A %B |
| | 0 70 30 |
| | 40 20 80 |
| | 50 20 80 |
| Flow rate: | 1 mL min⁻¹; |
| Detection (UV): | 210 nm; |
| Injection: | 10 μL; |
| Sample concentr.: | 1 mg mL⁻¹; |
| Instrumentation: | Merck KGaA - Hitachi (L6200) high |

-continued

| |
|---|
| pressure gradient pump system, Merck KGaA - Hitachi AS 2000 autosampler, Merck KGaA T 6300 column thermostat, Merck KGaA - Hitachi L 4500 developer. |

¹H-NMR, ¹³C-NMR and MS spectra are consistent with the structure.

E) [2S-(2R*,5R*,8R*,11R*)]-2,5,8,11-tetra(hydroxymethyl)-1,4,7,10-tetraazacyclododecane (THM-Cyclen)

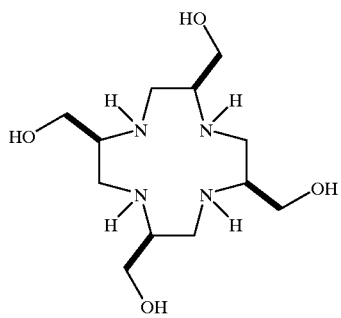

6.17 g (6.09 mmol) of the compound of the previous step were dissolved in dry MeOH (250 mL) and glacial $CH_3COOH$ (6 mL) in the presence of dry Pearlman catalyst $Pd(OH)_2$/C (commercial product) (9 g). The hydrogenation was then carried out under $N_2$ atmosphere with the aid of a Venturi stirrer, in 24 h. Water (200 mL) was added and the mixture was stirred for 24 h, then filtered through paper, then through a Millipore® 0.45 μm filter. Water and acetic acid were distilled off azeotropically with toluene. The resulting crude was dissolved in water (18 mL), loaded onto an Amberlite® IRA 400 ion exchange resin column (OH⁻ form, 33 mL) and eluted with water. Water was removed to obtain the desired compound (1.37 g; 4.69 mmol).
Yield: 77%.
m.p.: 160–225° C. (dec.)
¹H-NMR, ¹³C-NMR, IR and MS SPECTRA are consistent with the structure.
K.F.: 0.76%
Elemental analysis

| | C | H | N |
|---|---|---|---|
| Calc. % | 49.30 | 9.65 | 19.16 |
| Found % | 49.42 | 9.73 | 18.95 sulthe anhydrous |

Structure at the solid state: single crystals were obtained, which could be used for X-ray crystallography, by diffusion of acetone vapors in a THM-Cyclen concentrated aqueous solution. Crystal system: monoclinic; spacial group: C2; the molecule admits a two-fold symmetry axis, therefore the four stereogenic centres have the same absolute configuration.

| a [Å] | b [Å] | c [Å] | α [°] | β [°] | γ [°] | Z | R | wR2 |
|---|---|---|---|---|---|---|---|---|
| 18.217α | 4.659α | 10.262α | 90.0 | 123.36α | 90.0 | 2 | 0.042 | 0.12 |

F) [2S-(2R*,5R*,8R*,11R*)]-2,5,8,11-Tetra(hydroxymethyl)-1,4,7,10-tetraazacyclododecane-1,4,7,10-tetraacetic acid (THM-DOTA)

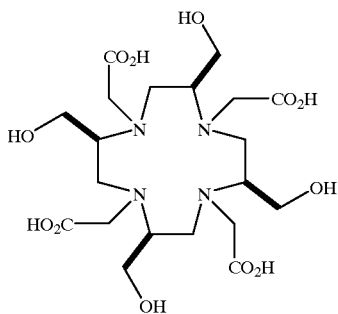

A solution of THM-Cyclen (12.38 g; 42.37 mmol) in water (500 mL), kept at 65° C., was added with $BrCH_2COOH$ (23.55 g; 169.5 mmol) in small portions during 2 h, dropping continuously 1.4 M $Me_4NOH$ (aq) by means of an Impulsomat-Dosimat apparatus, so as to keep a constant pH value of about 10. Further $BrCH_2COOH$ (20.28 g; 146.0 mmol) was added in decreasing amounts and the reaction was prolonged for a further 3 days.

The mixture was cooled on ice bath and pH was adjusted to 1.7 with 6N HCl (70 mL). The solution was concentrated to 350 mL, most tetramethylammonium salts were removed by repeated extractions with $CH_3CN$ (100 mL).

A content of 172 meq of undesired anions was calculated in the residual crude. A $NaHCO_3$ saturated solution (0.9N, 256 mL) was added until neutral pH; the mixture was concentrated (160 mL), loaded onto a Relite® 3AS/fb column ($HCO_3^-$ from; 165 mL) and eluted with water (flow: 220 mL/h). The homogeneous fractions were combined and concentrated (200 mL), then the solution (pH 9) was stirred in a beaker with Dowex® CCR3LB ($H^+$ form; 140 mL) for 1 h in a steam bath at 45° C. The resin was then filtered and washed with water, then regenerated (160 ml of resin were saturated with 1N HCl (1 L)), washed with water, then with 1N NaOH (200 mL) and again with water; finally regenerated with 1N HCl (1 L) (flow: 300 mL/h)). The treatment with the resin was repeated for a further 3 times, until $Me_4N^+$ cations were no longer detected by TLC (Dragendorff reagent, prepared according to: Stahl, E. *Dünnschicht Chromatographie—Ein Laboratoriumshandbuch* Springler-Verlag; Berlin-Göttingen-Heidelberg, 1962, page 504, n. 60) and a steady pH of about 3.6 was reached. Water was distilled off azeotropically with $CH_3CN$, to obtain the desired compound (11.98 g, 22.8 mmol).

Yield: 54%.
HPLC: 91% (area)—Method L/330 A

| | |
|---|---|
| Stationary phase: | Lichrospher 100 RP-18 5 μm; column 250 × 4 mm Merck KGaA; |
| Temperature: | 40° C.; |
| Mobile phase: | isocratic elution with premixed mobile phase: 1 g of n-octylamine was added to 181 mL of acetonitrile mixed with 819 mL of water. The solution is buffered to pH 6.0 with $H_3PO_4$; |
| Flow rate: | 1.3 mL $min^{-1}$; |
| Detection (UV): | 200 and 205 nm; |
| Injection: | 10 μL; |
| Sample concentr.: | 1 mg $mL^{-1}$; |
| Instrumentation: | Merck KGaA-Hitachi (L6200 and L6000) high pressure gradient pump system, Merck KGaA - Hitachi AS 2000 autosampler, Merck KGaA T 6300 column thermostat, Merck KGaA - Hitachi L 4250 UV detector. |

$^1$H-NMR, $^{13}$C-NMR, IR and MS spectra are consistent with the structure.
K.F.: 5.17%
Elemental analysis

| | C | H | N |
|---|---|---|---|
| Calc. % | 46.13 | 6.89 | 10.76 |
| Found % | 45.56 | 6.91 | 10.81 on anhydrous |

G) Gadolinium complex of [2S-(2R*,5R*,8R*,11R*)]-2,5,8,11-tetra(hydroxymethyl)-1,4,7,10-tetraazacyclododecane-1,4,7,10-tetraacetic acid sodium salt (1:1)

A solution of THM-DOTA (7.44 g; 14.29 mmol) in water (250 mL) was added with 14.37 mmol of $Gd(OAc)_3$. The mixture was heated at 60° C. for 20 h, then acetic acid and water were removed by repeated azeotropical distillations, first with toluene, then with $CH_3CN$. The residue was dissolved in water and pH was adjusted to 6.95 with 1N NaOH. This solution was slowly percolated (flow 22 mL/h) on a Dowex® CCR3LB column ($Na^+$ form; 18 mL). The eluates were collected and dried by azeotropical distillations with absolute EtOH, toluene, $CH_3OH$ to obtain the desired compound (9.45 g, 13.49 mmol).

Yield: 94%.
m.p.: 320–340° C. (dec)
HPLC: 89% (area)—Method L/330 A, Example 4F
IR and MS spectra are consistent with the structure.
K.F.: 9.09%
Loss weight (130° c): 9.39%
Elemental analysis:

| | C | H | Gd | N | Na |
|---|---|---|---|---|---|
| Calc. % | 34.28 | 4.60 | 22.44 | 8.00 | 3.28 ts |
| Found % | 33.79 | 4.82 | 21.38 | 7.64 | 3.46 |

The following compounds were obtained analogously:

dysprosium complex of [2S-(2R*,5R*,8R*,11R*)]-2,5,8,11-tetra(hydroxymethyl)-1,4,7,10-tetraazacyclododecane-1,4,7,10-tetraacetic acid sodium salt (1:1)

Gadolinium complex of [2S-(2R*,5R*,8R*,11R*)]-2,5,8,11-tetra(hydroxymethyl)-10-[2-[[2-(2-hydroxyethoxy)ethyl]amino]-2-oxoethyl]-1,4,7,10-tetraazacyclododecane-1,4,7-triacetic acid Dysprosium complex of [2S-(2R*,5R*,8R*,11R*)]-2,5,8,11-tetra(hydroxymethyl)-10-[2-[[2-(2-hydroxyethoxy)ethyl]amino]-2-oxoethyl]-1,4,7,10-tetraazacyclododecane-1,4,7-triacetic acid Gadolinium complex of [2S-(2R*,5R*,8R*,11R*)]-2,5,8,11-tetra(hydroxymethyl)-10-[2-(4-morpholinyl)-2-oxoethyl]-1,4,7,10-tetraazacyclododecane-1,4,7-triacetic acid Dysprosium complex of [2S-(2R*,5R*,8R*,11R*)]-2,5,8,11-tetra(hydroxymethyl)-10-[2-(4-morpholinyl)-2-oxoethyl]-1,4,7,10-tetraazacyclododecane-1,4,7-triacetic acid.

What is claimed is:

1. A compound of formula (I), in the racemic or in the optically active forms:

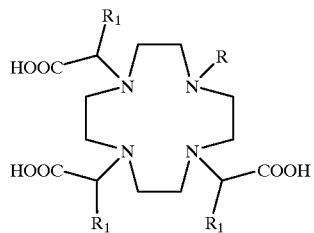

(I)

wherein:

R is

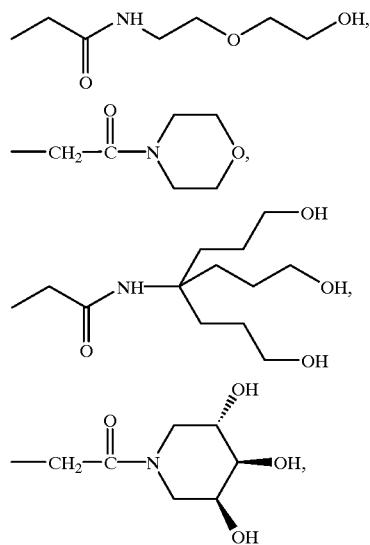

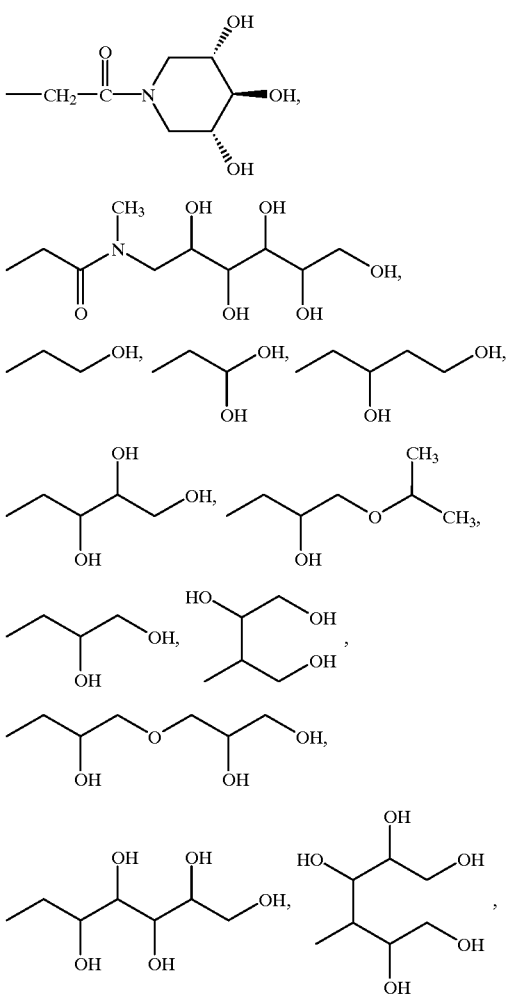

and each $R_1$, which can be the same or different, is a hydrogen atom or a —$CH_2OH$ group, as well as the chelated complexes of said compounds of formula (I) with the di- and trivalent ions of the metallic elements having atomic numbers ranging from 20 to 31, 39, from 42 to 44, 49 and from 57 to 83 and the physiologically acceptable salts thereof with organic bases selected from primary, secondary, tertiary amines or basic amino acids, or with inorganic bases the cations of which are sodium, potassium, magnesium, calcium, or mixtures thereof, or with anions of physiologically acceptable organic acids, selected from acetate, succinate, citrate, fumarate, maleate, oxalate, or with anions of physiologically acceptable inorganic acids selected from the anions of the hydrogen halides or the sulfate ions.

2. A compound of formula (II), in the racemic or the optically active form:

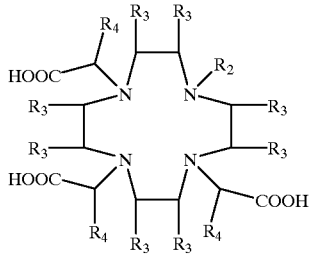

(II)

wherein:

$R_2$ is

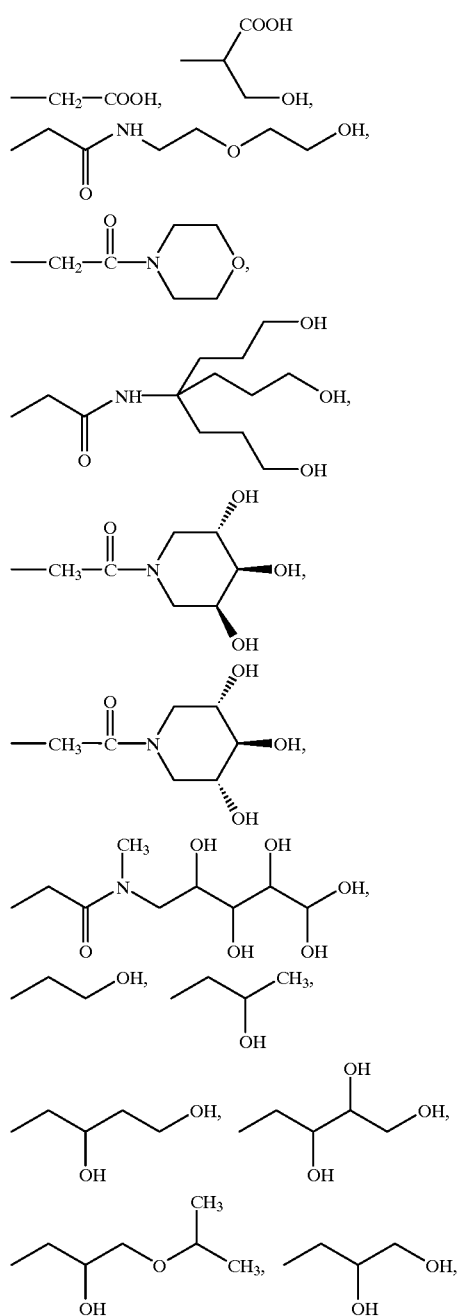

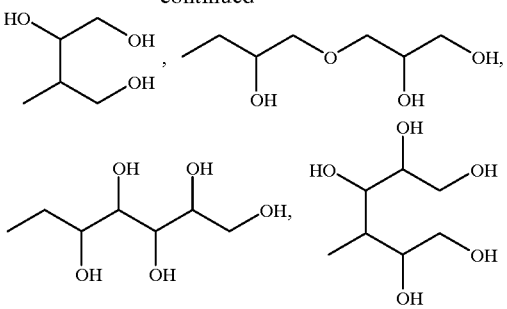

each $R_3$, which can be the same or different, is a hydrogen atom or a —$CH_2OH$ group, and each $R_4$, which can be the same or different, has the same meanings, as described for $R_3$ or is $CH_3$ or $C_2H_5$, as well as the chelated complexes of said compounds of formula (II) with the di- and trivalent ions of the metallic elements having atomic numbers ranging from 20 to 31, 39, from 42 to 44, 49 and from 57 to 83 and the physiologically acceptable salts thereof with organic bases selected from primary, secondary, tertiary amines or basic amino acids, or with inorganic bases the cations of which are sodium, potassium, magnesium, calcium, or mixtures thereof, or with anions of physiologically acceptable organic acids, selected from acetate, succinate, citrate, fumarate, maleate, oxalate, or with anions of physiologically acceptable inorganic acids selected from the anions of the halo acids or the sulfate ions.

3. A compound of formula (III), in the racemic or the optically active form:

(III)

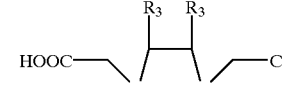

wherein:

Y is —OH, —NH—$CH_2$—$CH_2$—O—$CH_2$—$CH_2$—OH,

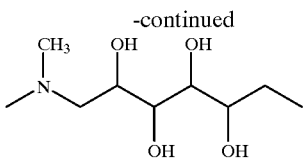

and each $R_3$, which can be the same or different, is a hydrogen atom or a —$CH_2OH$ group;

as well as the chelated complexes of said compounds of formula (III) with the di- and trivalent ions of the metallic elements having atomic numbers ranging from 20 to 31, 39, from 42 to 44, 49 and from 57 to 83 and the physiologically acceptable salts thereof with organic bases selected from primary, secondary, tertiary amines or basic amino acids, or with inorganic bases the cations of which are sodium, potassium, magnesium, calcium, or mixtures thereof, or with anions of physiologically acceptable organic acids, selected from acetate succinate, citrate, fumarate, maleate, oxalate, or with anions of physiologically acceptable inorganic acids selected from the anions of the halo acids or the sulfate ions.

4. A method of magnetic resonance imaging the organs or tissues of a human or animal body using a chelated complex of a compound of claim 1, 2 or 3.

5. Compounds according to claim 1, 2, or 3, in which the complexed di- or trivalent metal ion is selected from:
$Fe^{(2+)}$, $Fe^{(3+)}$, $Gd^{(3+)}$, $Eu^{(3+)}$, $Dy^{(3+)}$, $La^{(3+)}$, $Yb^{(3+)}$ and $Mn^{(2+)}$.

6. Compounds according to claim 1, 2, or 3, selected from the following group:
- 10-[2-[[2-(2-hydroxyethoxy)ethyl]amino]-2-oxoethyl]-α,α',α"-tris(hydroxymethyl)-1,4,7,10-tetraazacyclododecane-1,4,7-triacetic acid;
- α,α',α"-tris(hydroxymethyl)-10-(2-hydroxypropyl)-1,4,7,10-tetraazacyclododecane-1,4,7-triacetic acid;
- 2,9-bis(hydroxymethyl)-1,4,7,10-tetraazacyclododecane-1,4,7,10-tetraacetic acid;
- [2S-(2R*,5R*,8R*,11R*)]-2,5,8,11-tetra(hydroxymethyl)-1,4,7,10-tetraazacyclododecane-1,4,7,10-tetraacetic acid;
- 1-deoxy-1-[methyl-[1-oxo-2-[4,7,10-tris(1-carboxy-2-hydroxy-eth-1-yl)-1,4,7,10-tetraazacyclododec-1-yl]ethyl]amino]-D-glucitol;
- α,α',α"-tris(hydroxymethyl)-10-[2,3-dihydroxy-1-(hydroxymethyl)propyl]-1,4,7,10-tetraazacyclododecane-1,4,7-triacetic acid;
- [2S-(2R*,5R*,8R*,11R*)]-2,5,8,11-tetra(hydroxymethyl)-10-[2-[[2-(2-hydroxyethoxy)ethyl]amino]-2-oxoethyl]-1,4,7,10-tetraazacyclododecane-1,4,7-triacetic acid;
- [2S-(2R*,5R*,8R*,11R*)]-2,5,8,11-tetra(hydroxymethyl)-10-[2-(4-morpholinyl)-2-oxoethyl]-1,4,7,10-tetraazacyclododecane-1,4,7-triacetic acid.

7. A paramagnetic chelate, selected from the following group:
- gadolinium complex of 10-[2-[[2-(2-hydroxyethoxy)ethyl]amino]-2-oxoethyl]-α,α',α"-tris(hydroxymethyl)-1,4,7,10-tetraazacyclododecane-1,4,7-triacetic acid;
- gadolinium complex of α,α',α"-tris(hydroxymethyl)-10-(2-hydroxypropyl)-1,4,7,10-tetraazacyclododecane-1,4,7-triacetic acid;
- gadolinium complex of 2,9-bis(hydroxymethyl)-1,4,7,10-tetraazacyclododecane-1,4,7,10-tetraacetic acid salified with 1-deoxy-1-(methylamino)-D-glucitol (1:1);
- gadolinium complex of [2S-(2R*,5R*,8R*,11R*)]-2,5,8,11-tetra(hydroxymethyl)-1,4,7,10-tetraazacyclododecane-1,4,7,10-tetraacetic acid sodium salt (1:1);
- gadolinium complex of 1-deoxy-1-[methyl-[1-oxo-2-[4,7,10-tris(1-carboxy-2-hydroxy-eth-1-yl)-1,4,7,10-tetraazacyclododec-1-yl]ethyl]amino]-D-glucitol;
- gadolinium complex of α,α',α"-tris(hydroxymethyl)-10-[2,3-dihydroxy-1-(hydroxymethyl)propyl]-1,4,7,10-tetraazacyclododecane-1,4,7-triacetic acid;
- gadolinium complex of [2S-(2R*,5R*,8R*,11R*)]-2,5,8,11-tetra(hydroxymethyl)-10-[2-[[2-(2-hydroxyethoxy)ethyl]amino]-2-oxoethyl]-1,4,7,10-tetraazacyclododecane-1,4,7-triacetic acid;
- gadolinium complex of [2S-(2R*,5R*,8R*,11R*)]-2,5,8,11-tetra(hydroxymethyl)-10-[2-(4-morpholinyl)-2-oxoethyl]-1,4,7,10-tetraazacyclododecane-1,4,7-triacetic acid;
- dysprosium complex of 10-[2-[[2-(2-hydroxyethoxy)ethyl]amino]-2-oxoethyl]-α,α',α"-tris(hydroxymethyl)-1,4,7,10-tetraazacyclododecane-1,4,7-triacetic acid;
- dysprosium complex of α,α',α"-tris(hydroxymethyl)-10-(2-hydroxypropyl)-1,4,7,10-tetraazacyclododecane-1,4,7-triacetic acid;
- dysprosium complex of 2,9-bis(hydroxymethyl)-1,4,7,10-tetraazacyclododecane-1,4,7,10-tetraacetic acid salified with 1-deoxy-1-(methylamino)-D-glucitol (1:1);
- dysprosium complex of [2S-(2R*,5R*,8R*,11R*)]-2,5,8,11-tetra(hydroxymethyl)-1,4,7,10-tetraazacyclododecane-1,4,7,10-tetraacetic acid sodium salt (1:1);
- dysprosium complex of 1-deoxy-1-[methyl-[1-oxo-2-[4,7,10-tris(1-carboxy-2-hydroxy-eth-1-yl)-1,4,7,10-tetraazacyclododec-1-yl]ethyl]amino]-D-glucitol;
- dysprosium complex of α,α',α"-tris(hydroxymethyl)-10-[2,3-dihydroxy-1-(hydroxymethyl)propyl]-1,4,7,10-tetraazacyclododecane-1,4,7-triacetic acid;
- dysprosium complex of [2S-(2R*,5R*,8R*,11R*)]-2,5,8,11-tetra(hydroxymethyl)-10-[2-[[2-(2-hydroxyethoxy)ethyl]amino]-2-oxoethyl]-1,4,7,10-tetraazacyclododecane-1,4,7-triacetic acid;
- dysprosium complex of [2S-(2R*,5R*,8R*,11R*)]-2,5,8,11-tetra(hydroxymethyl)-10-[2-(4-morpholinyl)-2-oxoethyl]-1,4,7,10-tetraazacyclododecane-1,4,7-triacetic acid.

8. Diagnostic pharmaceutical composition for M.R.I., comprising at least one of the chelated complexes according to claim 1, 2 or 3 or a physiologically acceptable salt thereof.

* * * * *